United States Patent
Jha et al.

(10) Patent No.: US 9,827,272 B2
(45) Date of Patent: Nov. 28, 2017

(54) GROWTH FACTOR SEQUESTERING AND PRESENTING HYDROGELS

(71) Applicant: The Regents of the University of California, Oakland, CA (US)

(72) Inventors: Amit Kumar Jha, Oakland, CA (US); Kevin E. Healy, Moraga, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/760,141

(22) PCT Filed: Jan. 16, 2014

(86) PCT No.: PCT/US2014/011862
§ 371 (c)(1),
(2) Date: Jul. 9, 2015

(87) PCT Pub. No.: WO2014/113573
PCT Pub. Date: Jul. 24, 2014

(65) Prior Publication Data
US 2015/0352156 A1    Dec. 10, 2015

Related U.S. Application Data

(60) Provisional application No. 61/753,834, filed on Jan. 17, 2013, provisional application No. 61/781,777, filed on Mar. 14, 2013.

(51) Int. Cl.
| | |
|---|---|
| *C07K 14/495* | (2006.01) |
| *A61K 35/44* | (2015.01) |
| *A61K 38/18* | (2006.01) |
| *A61K 9/00* | (2006.01) |
| *A61K 47/48* | (2006.01) |
| *C12N 5/00* | (2006.01) |
| *A61K 35/12* | (2015.01) |

(52) U.S. Cl.
CPC ............ *A61K 35/44* (2013.01); *A61K 9/0019* (2013.01); *A61K 38/1841* (2013.01); *A61K 47/4823* (2013.01); *A61K 47/48246* (2013.01); *A61K 47/48338* (2013.01); *A61K 47/48784* (2013.01); *C07K 14/495* (2013.01); *C12N 5/0068* (2013.01); *A61K 2035/124* (2013.01); *A61K 2035/128* (2013.01); *C12N 2501/91* (2013.01); *C12N 2533/50* (2013.01); *C12N 2533/70* (2013.01); *C12N 2533/80* (2013.01)

(58) Field of Classification Search
None
See application file for complete search history.

(56) References Cited

U.S. PATENT DOCUMENTS

| | | |
|---|---|---|
| 2007/0026518 A1 | 2/2007 | Healy et al. |
| 2011/0033543 A1* | 2/2011 | Kiick ................... A61K 9/1641 424/484 |
| 2012/0225814 A1 | 9/2012 | Hanjaya-Putra et al. |

FOREIGN PATENT DOCUMENTS

| | | |
|---|---|---|
| WO | WO 00/64481 A1 | 11/2000 |
| WO | WO 2010/019769 A1 | 2/2010 |
| WO | WO 2011/163069 A2 | 12/2011 |

OTHER PUBLICATIONS

Censi et al., "Hydrogels for protein delivery in tissue engineering", Journal of Controlled Release, Mar. 2, 2012, pp. 680-692, vol. 161, No. 2, Elsevier, Amsterdam, Netherlands.
Jeon et al., "Affinity-based growth factor delivery using biodegradable, photocrosslinked heparin-alginate hydrogels", Journal of Controlled Release, Jun. 18, 2011, pp. 258-266, vol. 154, No. 3, Elsevier, Amsterdam, Netherlands.
Kim et al., "Hydrogel design for cartilage tissue engineering: A case study with hyaluronic acid", Biomaterials, Aug. 23, 2011, pp. 8771-8782, vol. 32, No. 34, Elsevier Science Publishers BV., Barking, Great Britain.
Rizzi, Simone C. et al. "Recombinant protein-co-PEG networks as cell-adhesive and proteolytically degradable hydrogel matrixes. Part I: development and physicochemical characteristics", Biomacromolecules, 2005, vol. 6, No. 3, pp. 1226-1238.
Slaughter, Brandon V. et al. "Hydrogels in regenerative medicine", Advanced Materials, 2009, vol. 21, Nos. 32-33, pp. 3307-3329.

\* cited by examiner

*Primary Examiner* — Jeanette Lieb
(74) *Attorney, Agent, or Firm* — Bozicevic Field & Francis, LLP; Paula A. Borden

(57) ABSTRACT

Provided herein are hydrogel cell matrices, hydrogel cell matrix systems for the support, growth, and differentiation of a stem cell or progenitor cell and methods for making such hydrogel cell matrices.

25 Claims, 28 Drawing Sheets

SEQUENCE LISTING

<160> NUMBER OF SEQ ID NOS: 48

<210> SEQ ID NO 1
<211> LENGTH: 16
<212> TYPE: PRT
<213> ORGANISM: Artificial Sequence

```
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 1

Cys Cys Gly Gly Asn Gly Glu Pro Arg Gly Asp Thr Tyr Arg Ala Tyr
1               5                   10                  15

<210> SEQ ID NO 2
<211> LENGTH: 8
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 2

Cys Phe His Arg Arg Ile Lys Ala
1               5

<210> SEQ ID NO 3
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: The amino acid residue at this position may be
      present or absent.
<220> FEATURE:
<221> NAME/KEY: MOD_RES
<222> LOCATION: (2)..(2)
<223> OTHER INFORMATION: In cases where residue 1 is absent this residue
      may be modified by ACETYLATION
<220> FEATURE:
<221> NAME/KEY: MOD_RES
<222> LOCATION: (16)..(16)
<223> OTHER INFORMATION: AMIDATION

<400> SEQUENCE: 3

Cys Cys Gly Gly Asn Gly Glu Pro Arg Gly Asp Thr Tyr Arg Ala Tyr
1               5                   10                  15

<210> SEQ ID NO 4
<211> LENGTH: 11
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: The amino acid residue at this position may be
      present or absent.
<220> FEATURE:
```

<221> NAME/KEY: MOD_RES
<222> LOCATION: (2)..(2)
<223> OTHER INFORMATION: In cases where residue 1 is absent this residue
      may be modifed by ACETYLATION
<220> FEATURE:
<221> NAME/KEY: MOD_RES
<222> LOCATION: (10)..(10)
<223> OTHER INFORMATION: AMIDATION

<400> SEQUENCE: 4

Cys Cys Gly Gly Phe His Arg Arg Ile Lys Ala
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 5

Cys Cys Glu Pro Arg Gly Asp Thr Tyr Arg Ala Tyr Gly
1               5                   10

<210> SEQ ID NO 6
<211> LENGTH: 13
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 6

Cys Cys Gly Gly Gly Glu Ala Pro Arg Gly Asp Val Tyr
1               5                   10

<210> SEQ ID NO 7
<211> LENGTH: 11
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 7

Cys Cys Cys Gly Pro Arg Gly Asp Val Tyr Gly
1               5                   10

<210> SEQ ID NO 8
<211> LENGTH: 19
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be -continued present or absent.

<400> SEQUENCE: 8

Cys Cys Gly Gly Val Ser Trp Phe Ser Arg His Arg Tyr Ser Pro Phe
1               5                   10                  15

Ala Val Ser

<210> SEQ ID NO 9
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 9

Cys Cys Gly Gly Asn Arg Trp His Ser Ile Tyr Ile Thr Arg Phe Gly
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 10

Cys Cys Gly Gly Thr Trp Tyr Lys Ile Ala Phe Gln Arg Asn Arg Lys
1               5                   10                  15

<210> SEQ ID NO 11
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 11

Cys Cys Gly Gly Arg Lys Arg Leu Gln Val Gln Leu Ser Ile Arg Thr
1               5                   10                  15

<210> SEQ ID NO 12
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 12

Cys Cys Gly Gly Lys Ala Phe Asp Ile Thr Tyr Val Arg Leu Lys Phe

```
<210> SEQ ID NO 13
<211> LENGTH: 11
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 13

Cys Cys Thr Arg Lys Lys His Asp Asn Ala Gln
1               5                   10

<210> SEQ ID NO 14
<211> LENGTH: 16
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 14

Cys Val Ser Trp Phe Ser Arg His Arg Tyr Ser Pro Phe Ala Val Ser
1               5                   10                  15

<210> SEQ ID NO 15
<211> LENGTH: 11
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 15

Cys Arg Asn Ile Ala Glu Ile Ile Lys Asp Ile
1               5                   10

<210> SEQ ID NO 16
<211> LENGTH: 13
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 16

Cys Thr Ala Gly Ser Cys Leu Arg Lys Phe Ser Thr Met
1               5                   10

<210> SEQ ID NO 17
<211> LENGTH: 11
<212> TYPE: PRT
<213> ORGANISM: Artificial sequence
```

```
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 17

Cys Thr Thr Ser Trp Ser Gln Cys Ser Lys Ser
1               5                   10

<210> SEQ ID NO 18
<211> LENGTH: 14
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 18

Cys Arg Tyr Val Val Leu Pro Arg Pro Val Cys Phe Glu Lys
1               5                   10

<210> SEQ ID NO 19
<211> LENGTH: 6
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid residue at this position may be
      present or absent.

<400> SEQUENCE: 19

Cys Glu Val Leu Leu Ile
1               5

<210> SEQ ID NO 20
<211> LENGTH: 4
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: the amino acids in this position can be any
      amino acid
<220> FEATURE:
<221> NAME/KEY: MISC_FEATURE
<222> LOCATION: (4)..(4)
<223> OTHER INFORMATION: the amino acids in this position can be any
      hydrophobic amino acid

<400> SEQUENCE: 20

Pro Xaa Xaa Xaa
1

<210> SEQ ID NO 21
<211> LENGTH: 5
<212> TYPE: PRT
<213> ORGANISM: Artificial sequence
<220> FEATURE:
<223> OTHER INFORMATION: synthetic polypeptide
```

```
<220> FEATURE:
<221> NAME/KEY: MISC_FEATURE
<222> LOCATION: (2)..(3)
<223> OTHER INFORMATION: the amino acid in this position can be any
      amino acid
<220> FEATURE:
<221> NAME/KEY: MISC_FEATURE
<222> LOCATION: (4)..(4)
<223> OTHER INFORMATION: the amino acid in this position can be any
      hydrophobic amino acid
<220> FEATURE:
<221> NAME/KEY: MISC_FEATURE
<222> LOCATION: (5)..(5)
<223> OTHER INFORMATION: the amino acid in this position can be either
      Ser or Thr

<400> SEQUENCE: 21

Pro Xaa Xaa Xaa Xaa
1               5

<210> SEQ ID NO 22
<211> LENGTH: 6
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Xaa is either Leu or Gln

<400> SEQUENCE: 22

Pro Xaa Gly Met Thr Ser
1               5

<210> SEQ ID NO 23
<211> LENGTH: 5
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Xaa is either Leu or Gln

<400> SEQUENCE: 23

Pro Xaa Gly Met Thr
1               5

<210> SEQ ID NO 24
<211> LENGTH: 10
<212> TYPE: PRT
<213> ORGANISM: Artificial sequence
<220> FEATURE:
<223> OTHER INFORMATION: synthetic polypeptide

<400> SEQUENCE: 24

Cys Gly Leu Val Pro Ala Gly Ser Gly Pro
1               5                   10

<210> SEQ ID NO 25
<211> LENGTH: 12
<212> TYPE: PRT
<213> ORGANISM: Artificial sequence
<220> FEATURE:
<223> OTHER INFORMATION: synthetic polypeptide

<400> SEQUENCE: 25

Ser Leu Leu Lys Ser Arg Met Val Pro Asn Phe Asn
```

<210> SEQ ID NO 26
<211> LENGTH: 12
<212> TYPE: PRT
<213> ORGANISM: Artificial sequence
<220> FEATURE:
<223> OTHER INFORMATION: synthetic polypeptide

<400> SEQUENCE: 26

Ser Leu Leu Ile Ala Arg Arg Met Pro Asn Phe Asn
1               5                   10

<210> SEQ ID NO 27
<211> LENGTH: 12
<212> TYPE: PRT
<213> ORGANISM: Artificial sequence
<220> FEATURE:
<223> OTHER INFORMATION: synthetic polypeptide

<400> SEQUENCE: 27

Ser Lys Leu Val Gln Ala Ser Ala Ser Gly Val Asn
1               5                   10

<210> SEQ ID NO 28
<211> LENGTH: 12
<212> TYPE: PRT
<213> ORGANISM: Artificial sequence
<220> FEATURE:
<223> OTHER INFORMATION: synthetic polypeptide

<400> SEQUENCE: 28

Ser Ser Tyr Leu Lys Ala Ser Asp Ala Pro Asp Asn
1               5                   10

<210> SEQ ID NO 29
<211> LENGTH: 12
<212> TYPE: PRT
<213> ORGANISM: Artificial sequence
<220> FEATURE:
<223> OTHER INFORMATION: synthetic polypeptide

<400> SEQUENCE: 29

Arg Pro Lys Pro Gln Gln Phe Phe Gly Leu Met Asn
1               5                   10

<210> SEQ ID NO 30
<211> LENGTH: 12
<212> TYPE: PRT
<213> ORGANISM: Artificial sequence
<220> FEATURE:
<223> OTHER INFORMATION: synthetic polypeptide

<400> SEQUENCE: 30

Ser Leu Arg Pro Leu Ala Leu Trp Arg Ser Phe Asn
1               5                   10

<210> SEQ ID NO 31
<211> LENGTH: 12
<212> TYPE: PRT
<213> ORGANISM: Artificial sequence
<220> FEATURE:
<223> OTHER INFORMATION: synthetic polypeptide

<400> SEQUENCE: 31

Ser Pro Gln Gly Ile Ala Gly Gln Arg Asn Phe Asn
1               5                   10

<210> SEQ ID NO 32
<211> LENGTH: 14
<212> TYPE: PRT
<213> ORGANISM: Artificial sequence
<220> FEATURE:
<223> OTHER INFORMATION: synthetic polypeptide

<400> SEQUENCE: 32

Asp Val Asp Glu Arg Asp Val Arg Gly Phe Ala Ser Phe Leu
1               5                   10

<210> SEQ ID NO 33
<211> LENGTH: 12
<212> TYPE: PRT
<213> ORGANISM: Artificial sequence
<220> FEATURE:
<223> OTHER INFORMATION: synthetic polypeptide

<400> SEQUENCE: 33

Ser Leu Pro Leu Gly Leu Trp Ala Pro Asn Phe Asn
1               5                   10

<210> SEQ ID NO 34
<211> LENGTH: 12
<212> TYPE: PRT
<213> ORGANISM: Artificial sequence
<220> FEATURE:
<223> OTHER INFORMATION: synthetic polypeptide

<400> SEQUENCE: 34

Ser Leu Leu Ile Phe Arg Ser Trp Ala Asn Phe Asn
1               5                   10

<210> SEQ ID NO 35
<211> LENGTH: 12
<212> TYPE: PRT
<213> ORGANISM: Artificial sequence
<220> FEATURE:
<223> OTHER INFORMATION: synthetic polypeptide

<400> SEQUENCE: 35

Ser Gly Val Val Ile Ala Thr Val Ile Val Ile Thr
1               5                   10

<210> SEQ ID NO 36
<211> LENGTH: 12
<212> TYPE: PRT
<213> ORGANISM: Artificial sequence
<220> FEATURE:
<223> OTHER INFORMATION: synthetic polypeptide

<400> SEQUENCE: 36

Ser Leu Gly Pro Gln Gly Ile Trp Gly Gln Phe Asn
1               5                   10

<210> SEQ ID NO 37
<211> LENGTH: 12
<212> TYPE: PRT
<213> ORGANISM: Artificial sequence
<220> FEATURE:
<223> OTHER INFORMATION: synthetic polypeptide

<400> SEQUENCE: 37

Lys Lys Ser Pro Gly Arg Val Val Gly Gly Ser Val
1               5                   10

```
<210> SEQ ID NO 38
<211> LENGTH: 12
<212> TYPE: PRT
<213> ORGANISM: Artificial sequence
<220> FEATURE:
<223> OTHER INFORMATION: synthetic polypeptide

<400> SEQUENCE: 38

Pro Gln Gly Leu Leu Gly Ala Pro Gly Ile Leu Gly
1               5                   10

<210> SEQ ID NO 39
<211> LENGTH: 31
<212> TYPE: PRT
<213> ORGANISM: Artificial sequence
<220> FEATURE:
<223> OTHER INFORMATION: synthetic polypeptide

<400> SEQUENCE: 39

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 40
<211> LENGTH: 12
<212> TYPE: PRT
<213> ORGANISM: Artificial sequence
<220> FEATURE:
<223> OTHER INFORMATION: synthetic polypeptide

<400> SEQUENCE: 40

Gly Pro Gln Gly Leu Ala Gly Gln Arg Gly Ile Val
1               5                   10

<210> SEQ ID NO 41
<211> LENGTH: 12
<212> TYPE: PRT
<213> ORGANISM: Artificial sequence
<220> FEATURE:
<223> OTHER INFORMATION: synthetic polypeptide

<400> SEQUENCE: 41

Gly Gly Ser Gly Gln Arg Gly Arg Lys Ala Leu Glu
1               5                   10

<210> SEQ ID NO 42
<211> LENGTH: 12
<212> TYPE: PRT
<213> ORGANISM: Artificial sequence
<220> FEATURE:
<223> OTHER INFORMATION: synthetic polypeptide

<400> SEQUENCE: 42

Ser Leu Ser Ala Leu Leu Ser Ser Asp Ile Phe Asn
1               5                   10

<210> SEQ ID NO 43
<211> LENGTH: 12
<212> TYPE: PRT
<213> ORGANISM: Artificial sequence
<220> FEATURE:
<223> OTHER INFORMATION: synthetic polypeptide

<400> SEQUENCE: 43

Ser Leu Pro Arg Phe Lys Ile Ile Gly Gly Phe Asn
```

```
<210> SEQ ID NO 44
<211> LENGTH: 12
<212> TYPE: PRT
<213> ORGANISM: Artificial sequence
<220> FEATURE:
<223> OTHER INFORMATION: synthetic polypeptide

<400> SEQUENCE: 44

Ser Leu Leu Gly Ile Ala Val Pro Gly Asn Phe Asn
1               5                   10

<210> SEQ ID NO 45
<211> LENGTH: 12
<212> TYPE: PRT
<213> ORGANISM: Artificial sequence
<220> FEATURE:
<223> OTHER INFORMATION: synthetic polypeptide

<400> SEQUENCE: 45

Phe Phe Lys Asn Ile Val Thr Pro Arg Thr Pro Pro
1               5                   10

<210> SEQ ID NO 46
<211> LENGTH: 9
<212> TYPE: PRT
<213> ORGANISM: Artificial sequence
<220> FEATURE:
<223> OTHER INFORMATION: synthetic polypeptide

<400> SEQUENCE: 46

Cys Gln Pro Gln Gly Leu Ala Lys Cys
1               5

<210> SEQ ID NO 47
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 47

Cys Gly Gly Glu Ile Leu Asp Val Pro Ser Thr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 48

Arg Asn Ile Ala Glu Ile Ile Lys Asp Ile Gly Cys
1               5                   10
```

US 9,827,272 B2

GROWTH FACTOR SEQUESTERING AND PRESENTING HYDROGELS

CROSS-REFERENCE

This application claims the benefit of U.S. Provisional Patent Application Nos. 61/753,834, filed Jan. 17, 2013, and 61/781,777, filed Mar. 14, 2013, which applications are incorporated herein by reference in their entirety.

STATEMENT REGARDING FEDERALLY SPONSORED RESEARCH

This invention was made with government support under Grant No. HL096525 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-205WO_ST25.txt" created on Jan. 15, 2014 and having a size of 15 KB. The contents of the text file are incorporated by reference herein in their entirety.

INTRODUCTION

Hydrogels are useful materials for a variety of biological applications.

SUMMARY

Provided herein are hydrogel cell matrices, hydrogel cell matrix systems for the support, growth, and differentiation of a stem cell or progenitor cell and methods for making such hydrogel cell matrices.

In one aspect provided herein is a hydrogel cell matrix that includes a plurality of hydrogel polymers; a cell adhesion peptide conjugated to one or more hydrogel polymers; and a cross-linker polymer that links one or more hydrogel polymers of the plurality of hydrogel polymers to another hydrogel polymer of the plurality. In certain embodiments, the hydrogel polymer is a hyaluronic acid (HyA) polymer. In specific embodiments, the hydrogel polymer is an acrylated hyaluronic acid (HyA) polymer. In specific embodiments, the cross-linker polymer is a thiolated cross linker peptide.

In one aspect provided herein is a hydrogel cell matrix that includes a plurality of hydrogel polymers; a cell adhesion peptide conjugated to one or more hydrogel polymers; and a cross-linker peptide that links one or more hydrogel polymers of the plurality of hydrogel polymers to another hydrogel polymer of the plurality. In certain embodiments, the hydrogel polymer is a hyaluronic acid (HyA) polymer. In specific embodiments, the hydrogel polymer is an acrylated hyaluronic acid (HyA) polymer. In specific embodiments, the cross-linker peptide is a thiolated cross linker peptide.

In one aspect provided herein is a hydrogel cell matrix that includes a plurality of hydrogel polymers; a cell adhesion peptide conjugated to one or more hydrogel polymers; and a proteolytically cleavable cross-linker peptide that links one or more hydrogel polymers of the plurality of hydrogel polymers to another hydrogel polymer of the plurality. In certain embodiments, the hydrogel polymer is a hyaluronic acid (HyA) polymer. In specific embodiments, the hydrogel polymer is an acrylated hyaluronic acid (HyA) polymer. In specific embodiments, the cross-linker peptide is a thiolated cross linker peptide.

In some embodiments, the hydrogel cell matrix includes a factor release molecule conjugated to one or more hydrogel polymers. In certain embodiments, the cell adhesion peptide and the factor release molecule are conjugated to the same hydrogel polymer. In other embodiments, the cell adhesion peptide and the factor release molecule are conjugated to different hydrogel polymers.

In certain embodiments, the cell adhesion peptide described herein includes the amino acid sequence RGD. In specific embodiments, the cell adhesion peptide has the amino acid sequence CGGNGEPRGDTYRAY (SEQ ID NO:1).

In certain embodiments of the hydrogel cell matrix, the factor release molecule is heparin. In specific embodiments, the factor release molecule allows for the controlled release or presentation of one or more growth factors. In certain embodiments, the factor release molecule is non-covalently bound to one or more growth factors. In specific embodiments, the growth factor is transforming growth factor-$\beta$ (TGF-$\beta$). In some embodiments, one or more growth factors are non-covalently bound to factor release molecules, and one or more of the growth factors were secreted by a cell cultured within the hydrogel cell matrix. In some embodiments, one or more growth factors are non-covalently bound to factor release molecules, and one or more of the growth factors were secreted by a cell not cultured within the hydrogel cell matrix. In another aspect, provided herein is a hydrogel cell matrix system that includes any one of the hydrogel cell matrices provided herein and a stem cell or progenitor cell encapsulated in the matrix. In certain embodiments, the hydrogel cell matrix system includes a cardiac progenitor cell (CPC).

In another aspect, provided herein is a method of making a hydrogel cell matrix comprising the steps of conjugating a cell adhesion peptide to a first hydrogel polymer; conjugating a factor release molecule to a second hydrogel polymer; and conjugating the first hydrogel polymer to the second hydrogel polymer using a cross-linker polymer, e.g., a cross-linker peptide, which may be a proteolytically cleavable cross-linker peptide. In certain embodiments the first and second hydrogel polymers are hyaluronic acid (HyA) polymers. In specific embodiments, the first and second hydrogel polymers are acrylated hyaluronic acid (HyA) polymer. In specific embodiments, the cross-linker peptide is a thiolated cross linker peptide. In certain embodiments, the cell adhesion peptide includes the amino acid sequence RGD. In specific embodiments, the cell adhesion peptide has the amino acid sequence CGGNGEPRGDTYRAY (SEQ ID NO:1). In certain embodiments, the factor release molecule is heparin.

In specific embodiments, the method further comprises the step of contacting factor release molecules with a growth factor, thereby producing a growth factor contacted hydrogel cell matrix. In certain embodiments, the growth factor is a transforming growth factor-$\beta$ (TGF-$\beta$). In some embodiments, the method comprises culturing a cell within the hydrogel cell matrix (or culturing a cell in the presence of factor release molecules conjugated to a hydrogel polymer), wherein proteins secreted by the cell non-covalently bind to the factor release molecules.

In another aspect, provided herein is a method of introducing a hydrogel cell matrix into a mammalian subject, comprising, prior to gelation, injecting a hydrogel cell matrix the present disclosure into the mammalian subject. In some cases, the hydrogel cell matrix comprises a growth factor non-covalently bound to the factor release molecule, wherein the factor release molecule allows for the release, presentation, or release and presentation of the growth factor. In some cases, the growth factor was secreted by a cell cultured on the hydrogel cell matrix.

The present disclosure provides a hydrogel cell matrix comprising: a) a plurality of hydrogel polymers; b) a cell adhesion peptide conjugated to one or more hydrogel polymers; c) a factor release molecule conjugated to one or more hydrogel polymers; and d) a cross-linker peptide that links one or more hydrogel polymers of the plurality of hydrogel polymers to another hydrogel polymer of the plurality. In some cases, the cross-linker peptide is a proteolytically cleavable cross-linker peptide. In some cases, the hydrogel polymer is a hyaluronic acid (HyA) polymer or an acrylated hyaluronic acid (HyA) polymer. In some cases, the cell adhesion peptide and the factor release molecule are conjugated to the same hydrogel polymer. In some cases, the cell adhesion peptide and the factor release molecule are conjugated to different hydrogel polymers. In some cases, the cell adhesion peptide comprises the amino acid sequence RGD. For example, in some cases, the cell adhesion peptide comprises the amino acid sequence CGGNGEPRGD-TYRAY (SEQ ID NO:1). In some cases, the factor release molecule is heparin. In some cases, a hydrogel cell matrix of the present disclosure further comprises a growth factor non-covalently bound to the factor release molecule, wherein the factor release molecule allows for the release, presentation, or release and presentation of the growth factor. In some cases, the growth factor is an exogenously added growth factor. For example, in some cases, the growth factor is selected from the group consisting of: transforming growth factor-β (TGF-β), vascular endothelial growth factor (VEGF), bone morphogenic protein-2 (BMP2), sonic hedgehog polypeptide (SHH), and fibroblast growth factor 21 (FGF21). In some cases, the growth factor is transforming growth factor-β (TGF-β). In some cases, the growth factor is one that is secreted by a cell cultured within the hydrogel cell matrix. In some cases, the cross-linked peptide is a thiolayted cross linker peptide. In some cases, the cross-linked peptide is cleavable by a matrix metalloproteinase (MMP). In some cases, In some cases, the MMP is MMP-13. In some cases, the cross-linked peptide is CQPQGLAKC (SEQ ID NO:46).

The present disclosure provides a hydrogel cell matrix system comprising the hydrogel cell matrix of claim 1 and a stem cell or progenitor cell encapsulated in the matrix. In some cases, the system comprises a progenitor cell. In some cases, the progenitor cell is a cardiac progenitor cell.

The present disclosure provides a method of making a hydrogel cell matrix comprising the steps of: (a) conjugating cell adhesion peptides to a first population of hydrogel polymers; (b) conjugating factor release molecules to a second population of hydrogel polymers; and (c) conjugating the first population of hydrogel polymers to the second population of hydrogel polymers using cross-linker peptides, thereby producing a hydrogel cell matrix. In some cases, the cross-linker peptides are proteolytically cleavable cross-linker peptides. In some cases, the method further comprises, after step (b), a step of contacting the factor release molecules with a growth factor, wherein the growth factor non-covalently binds to the factor release molecules, thereby producing a growth factor contacted hydrogel cell matrix. In some cases, the method further comprises culturing a cell on the growth factor contacted hydrogel cell matrix, wherein factors secreted by the cell non-covalently bind to the factor release molecules. In some cases, the method further comprises, after step (b), culturing a cell in the presence of the factor release molecules, wherein factors secreted by the cell non-covalently bind to the factor release molecules. In some cases, the method further comprises, after step (c), culturing a cell within the hydrogel cell matrix, wherein factors secreted by the cell non-covalently bind to the factor release molecules.

The present disclosure provides a method of introducing a hydrogel cell matrix into a mammalian subject, comprising, prior to gelation, injecting the hydrogel cell matrix of the present disclosure into the mammalian subject. In some cases, the hydrogel cell matrix comprises a growth factor non-covalently bound to the factor release molecule, wherein the factor release molecule allows for the release, presentation, or release and presentation of the growth factor. In some cases, the growth factor is one that is secreted by a cell cultured within the hydrogel cell matrix. In some cases, the hydrogel cell matrix comprises a stem cell or progenitor cell.

DEFINITIONS

Figure 1:
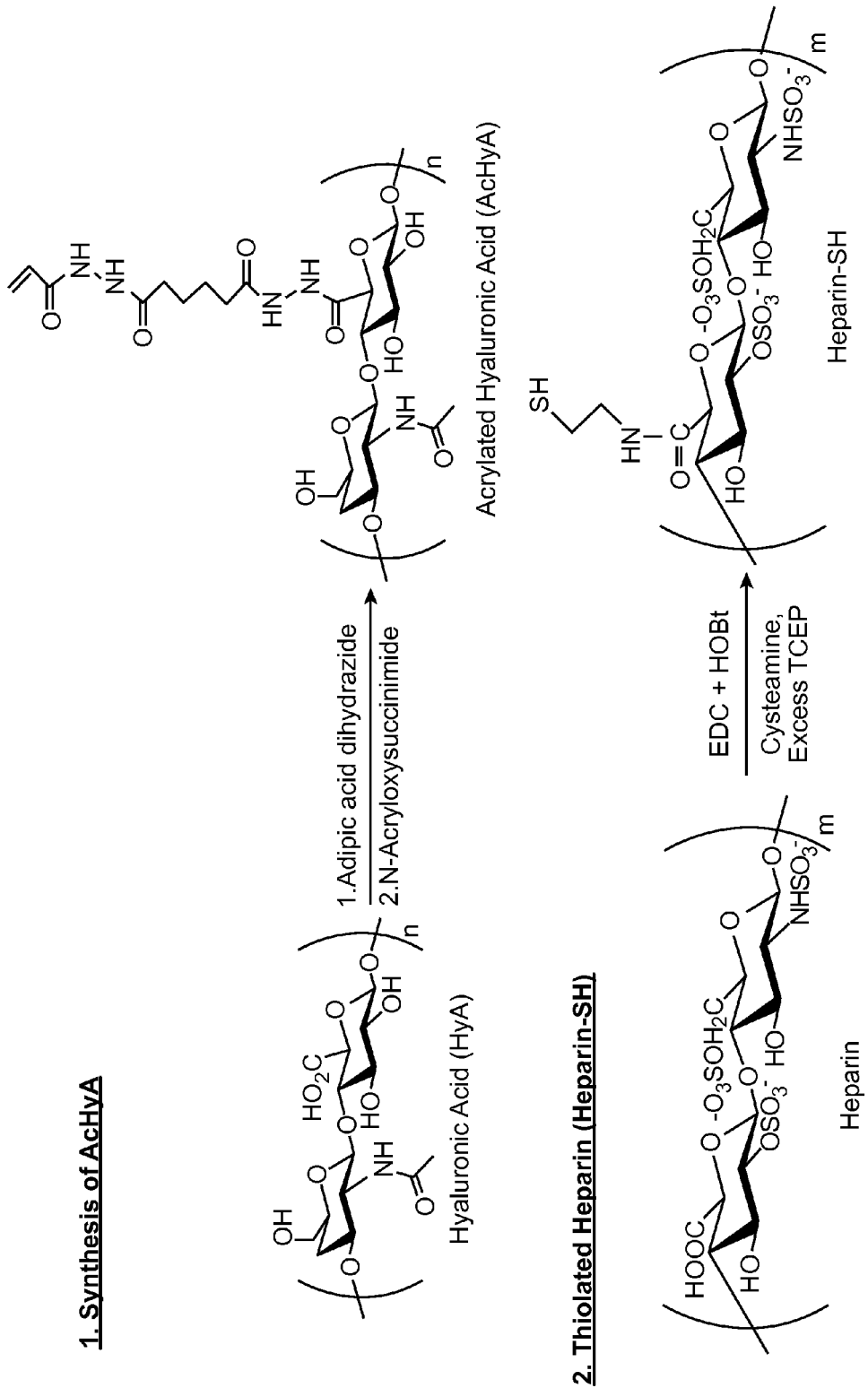
FIG. 1 shows an exemplary method of chemical synthesis of acrylated hyaluronic acid and an exemplary of synthesis of thiolated heparin.

The term "hydrogel cell matrix" as used herein refers to a network of polymer chains ("hydrogel polymers") that are water-insoluble, sometimes found as a colloidal gel in which water is the dispersion medium. Hydrogel cell matrices can contain over 99% water and may comprise natural or synthetic polymers, or a combination thereof. In other instances, hydrogels may contain other percentages of water, as described herein. Hydrogels also possess a degree of flexibility due to their significant water content.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a hydrogel" includes a plurality of such hydrogels and reference to "the cell adhesion peptide" includes reference to one or more cell adhesion peptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which, for brevity, are described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Provided herein are hydrogel cell matrices, hydrogel cell matrix systems for the support, growth, and differentiation of a stem cell or progenitor cell and methods for making such hydrogel cell matrices.

Hydrogel Cell Matrices and Systems

In one aspect provided herein is a hydrogel cell matrix that includes a plurality of hydrogel polymers; a cell adhesion peptide conjugated to one or more hydrogel polymers; a factor release molecule conjugated to one or more hydrogel polymers; and a cross-linker polymer (e.g., a cross-linker peptide; e.g., a proteolytically cleavable cross-linker peptide) that links one or more hydrogel polymers of the plurality of hydrogel polymers to another hydrogel polymer of the plurality. Such a hydrogel cell matrix allows for the survival, proliferation and function of a stem cell or progenitor cell (e.g., a cardiac progenitor cell (CPC)) encapsulated in the matrix.

Any suitable hydrogel polymers can be used in the hydrogel cell matrices provided herein. Hydro gel polymers may include the following monomers: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

The hydrogel polymer that encapsulates the stem cell or progenitor cell (e.g., a cardiac progenitor cell (CPC)) is generally hydrophilic. Suitable hydrogel polymers include, but are not limited to, poly(N-isopropylacrylamide) (pNIPAAm); poly(N-isopropylacrylamide-co-acrylic acid); hyaluronic acid or hyaluronate; crosslinked hyaluronic acid or hyaluronate; pHEMA; or copolymers of p(NIPAAm)-based sIPNs and other hydrogel sIPNs (semi-interpenetrating networks). In certain embodiments, the hydrogel polymer is a hyaluronic acid (HyA) polymer. In specific embodiments, the hydrogel polymer is an acrylated hyaluronic acid (HyA) polymer.

In some embodiments, the hydrogel is a temperature-sensitive hydrogel. In some embodiments, a temperature-sensitive hydrogel is a polyacrylic acid or derivative thereof, e.g., poly (N-isopropylacrylamide) gel, and the increase in temperature causes the hydrogel to contract, thereby forcing the active agent out of the hydrogel. Alternatively, the temperature-sensitive hydrogel is an interpenetrating hydrogel network of poly(acrylamide) and poly(acrylic acid), and the increase in temperature causes the hydrogel to swell, thereby allowing the active agent to diffuse out of the gel. The temperature required for triggering release of an active agent from the hydrogel is generally about normal body temperature, e.g., about 37° C.

One or more of the hydrogel polymers can be conjugated to a cell-adhesion moiety, e.g., a moiety that provides for binding to a cell-surface receptor. In specific embodiments, the cell-adhesion moiety is a cell adhesion ligand that provides for binding to a cell-surface receptor on the surface of a cell. In certain embodiments, the cell-binding moiety is a cell adhesion peptide. Any suitable cell adhesion peptide can be used. In certain embodiments, the cell adhesion peptide can bind an integrin. In specific embodiments, the cell adhesion peptide can bind 5β1 and or av β3 integrin. In specific embodiments, the cell adhesion molecule can promote angiogenesis.

In certain embodiments, the cell adhesion peptide has a length of 40 amino acids or less, 35 amino acids or less, 30 amino acids or less, 25 amino acids or less, or 20, 19, 18, 17, 16, 15, 14, 13, 12, 11, 10, 9, 8, 7, 6, or 5 amino acids or less. For example, in some cases, the cell adhesion peptide has a length of from about 3 amino acids to about 40 amino acids, e.g., from about 3 amino acids to about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, or from about 35 amino acids to about 40 amino acids.

The stiffness module of a subject hydrogel matrix can be in the range of from about 15 Pascals (Pa) to about 850 Pa, e.g., from about 15 Pa to about 20 Pa, from about 20 Pa to about 50 Pa, from about 50 Pa to about 100 Pa, from about 100 Pa to about 150 Pa, from about 150 Pa to about 200 Pa, from about 200 Pa to about 250 Pa, from about 250 Pa to about 300 Pa, from about 300 Pa to about 350 Pa, from about 350 Pa to about 400 Pa, from about 400 Pa to about 500 Pa, from about 500 Pa to about 600 Pa, from about 600 Pa to about 700 Pa, from about 700 Pa to about 800 Pa, or from about 800 Pa to about 850 Pa.

The concentration of peptides in a subject hydrogel matrix can range from about 50 μM to about 500 μM, e.g., from about 50 μM to about 75 μM, from about 75 μM to about 100 μM, from about 100 μM to about 125 μM, from about 125 μM to about 150 μM, from about 150 μM to about 200 μM, from about 200 μM to about 250 μM, from about 250 μM to about 300 μM, from about 300 μM to about 350 μM, from about 350 μM to about 400 μM, from about 400 μM to about 450 μM, or from about 450 μM to about 500 μM.

In specific embodiments, the cell adhesion peptide is an Arg-Gly-Asp (RGD) peptide (i.e., a peptide that contains the amino acid sequence RGD). A suitable RGD peptide comprises the amino acid sequence: CGGNGEPRGDTYRAY (SEQ ID NO:1). Also suitable for use are peptides comprising the amino acid sequence FHRRIKA (SEQ ID NO:2). Also suitable for use are the peptides acetyl-CG-GNGEPRGDTYRAY-NH$_2$ (SEQ ID NO:3) and acetyl-CG-GFHRRIKA-NH$_2$ (SEQ ID NO:4). Other suitable peptides are shown in Table 1, below.

TABLE 1

| Peptide | SEQ ID NO: |
|---|---|
| CGGNGEPRGDTYRAY | SEQ ID NO: 1 |
| CEPRGDTYRAYG | SEQ ID NO: 5 |
| CGGGEAPRGDVY | SEQ ID NO: 6 |
| CCGPRGDVYG | SEQ ID NO: 7 |
| CGGVSWFSRHRYSPFAVS | SEQ ID NO: 8 |
| CGGNRWHSIYITRFG | SEQ ID NO: 9 |
| CGGTWYKIAFQRNRK | SEQ ID NO: 10 |
| CGGRKRLQVQLSIRT | SEQ ID NO: 11 |
| CGGKAFDITYVRLKF | SEQ ID NO: 12 |
| CTRKKHDNAQ | SEQ ID NO: 13 |
| VSWFSRHRYSPFAVS | SEQ ID NO: 14 |
| RNIAEIIKDI | SEQ ID NO: 15 |
| TAGSCLRKFSTM | SEQ ID NO: 16 |
| TTSWSQCSKS | SEQ ID NO: 17 |
| RYVVLPRPVCFEK | SEQ ID NO: 18 |
| EVLLI | SEQ ID NO: 19 |

In some cases, the cell adhesion peptide has an additional cysteine residue added to the N-terminal side of the peptide to allow for conjugation of the peptide to a second moiety (e.g., to allow for conjugation of the peptide to a hydrogel polymer). In some instances, a peptide represented by one of the sequences set forth in SEQ ID NO:1-19 may have a cysteine residue added to the N terminal side of the sequence. In certain embodiments, the cell adhesion peptide has the amino acid sequence CGGNGEPRGDTYRAY (SEQ ID NO: 1).

One or more of the hydrogel polymers can be conjugated to a factor release molecule that allows for the controlled release and delivery of a factor non-covalently bound to the factor release molecule at a predictable rate. In some cases, a fraction (e.g., 10%, 20%, 30%, 40%, 50%, 60%, 70%, 80%, 90%, or 100%) of factors (e.g., a population of factors, where all members of the population are the same type of factor or where the population comprises two or more different factors) that are non-covalently bound to the factor release molecules are "released" (i.e., are no longer bound to the factor release molecule) over time (e.g., over a period of 7 days, 10 days, 12 days, 15 days, 20 days, 25 days, or 30 days). In some cases, the rate of factor release is predictable (e.g., the rate has already been calculated for a particular factor in combination with a particular hydrogel matrix or particular release factor). In some cases, the rate of factor release can be controlled (e.g., experimentally manipulated) using methods known by one of ordinary skill in the art (e.g., using a cleavable linker to bind the factor to the factor release molecule, using a molecule to out-compete the factor for binding to the factor release molecule, etc.). Cells being cultured within the hydrogel matrix are then exposed to (i.e., are contacted with, are free to bind to) the released factors.

The weight percent of the factor release molecule in the hydrogel matrix can range from 0.01 weight % to about 1 weight %, e.g., 0.01 weight %, 0.02 weight %, 0.03 weight %, 0.04 weight %, 0.05 weight %, from 0.05 weight % to about 0.1 weight %, from about 0.1 weight % to about 0.25 weight %, from about 0.25 weight % to about 0.5 weight %, from about 0.5 weight % to about 0.75 weight %, or from about 0.75 weight % to 1 weight %.

In some cases, cells being cultured on the hydrogel matrix can bind to factors that are still non-covalently bound to the factor release molecules. Thus, the factor release molecule, and therefore the hydrogel matrix, can be said to "present" a factor (e.g., a factor that is non-covalently bound to the factor release molecule) to a cell.

Any suitable factor release molecules may be used. In specific embodiments, the factor release molecule can regulate thrombosis and/or blood vessel formation. In some embodiments, the factor release molecule is a polysaccharide. In specific embodiments, the factor release molecule is glycosaminoglycan. In specific embodiments, the factor release molecule is heparin.

In certain embodiments, the hydrogel cell matrix includes one or more factors that can be bound to, released and delivered ("presented") to a cell encapsulated by the hydrogel cell matrix in a controlled manner. Factors that are bound and released by the factor release molecule can be any factor that modulates (e.g., increases or decreases) the growth, proliferation, survival, differentiation (e.g., a factor that promotes differentiation; a factor that inhibits differentiation; a factor that reverses differentiation, e.g., a de-differentiation factor, a pluripotency factor, etc.; and the like), and/or function of a cell encapsulated by the hydrogel cell matrix. As used herein, the term "growth factor" is used broadly to encompass factors that modulate the growth, proliferation, survival, differentiation, and/or function of a cell. Suitable growth factors include, but are not limited to: a colony stimulating factor (e.g., Neupogen® (filgrastim, G-CSF), Neulasta (pegfilgrastim), granulocyte colony stimulating factor (G-CSF), granulocyte-monocyte colony stimulating factor, macrophage colony stimulating factor, megakaryocyte colony stimulating factor, and the like), a growth hormone (e.g., a somatotropin, e.g., Genotropin®, Nutropin®, Norditropin®, Saizen®, Serostim®, Humatrope®, a human growth hormone, and the like), an interleukin (e.g., IL-1, IL-2, including, e.g., Proleukin®, IL-3, IL-4, IL-5, IL-6, IL-7, IL-8, IL-9, etc.), a growth factor (e.g., Regranex® (beclapermin, PDGF), Fiblast® (trafermin, bFGF), Stemgen® (ancestim, stem cell factor), keratinocyte growth factor, an acidic fibroblast growth factor, a stem cell factor, a basic fibroblast growth factor, a hepatocyte growth factor (HGF), and the like), a chemokine (e.g., IP-10, Mig, Groα/IL-8, RANTES, MIP-1α, MIP-1β, MCP-1, PF-4, and the like), an angiogenic agent (e.g., vascular endothelial growth factor (VEGF)), an EGF (epidermal growth factor), a receptor tyrosine kinase ligand, thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases, a vasoactive intestinal peptide, angiogenin, angiotropin, fibrin, hirudin, a leukemia inhibitory factor, a Wnt signaling ligand (e.g., Wnt, norrin, R-spondin, etc.), a Wnt signaling inhibitor (e.g, WIF (Wnt inhibitory factor), sFRP (Secreted Frizzled Related Protein), Dkk (Dickkopf), Notum, and the like), a Notch or Notch ligand protein, a receptor tyrosine kinase ligand, a hedgehog (HH) pathway ligand (e.g., HH), and a transforming growth factor-β (TGF-β). In certain embodiments, the factor is a cell growth factor. In specific embodiments, the factor is a growth factor that promotes the growth of a cardiac progenitor cell. In specific embodiments, the factor is transforming growth factor-β (TGF-β).

In some embodiments, it is unknown which growth factor or factors are bound to the factor release molecule. As a non-limiting example, cells can be grown (i.e., cultured) on a subject hydrogel matrix for any convenient amount of time (e.g., 5 minutes to 2 weeks, e.g., 5-30 minutes, 5 minutes, 10 minutes, 15 minutes, 20 minutes, 30 minutes, 30 minutes to 1 hour, 1 hour, 1-2 hours, 2 hours, 1-3 hours, 3 hours, 2-4 hours, 4 hours, 3-5 hours, 5 hours, 4-6 hours, 6 hours, 8 hours, 10 hours, 12-24 hours, 12 hours, 18 hours, 24 hours, 24-36 hours, 36 hours, 36-48, 48 hours, 2 days-1 week, 2 days, 3 days, 4 days, 5 days, 6 days, 1 week, 1-2 weeks, or 2 weeks) in any desired condition. As cells secrete many known and/or unknown factors, the factors non-covalently bind to the factor release molecules of the hydrogel matrix (or factor release molecules conjugated to a hydrogel polymer). Thus, cells can be cultured on a subject hydrogel matrix to "prime" or "load" the hydrogel matrix with secreted factors. Those factors can subsequently be released or presented. In some embodiments, the cell-secreted factors are known. In some embodiments, the cell-secreted factors are unknown. In some embodiments, the cell-secreted factors are a mixture of known and unknown factors. In some embodiments, a cell is cultured on a hydrogel matrix comprising factor release molecules non-covalently bound to one or more known factor(s) (e.g., a growth factor, e.g., TGF-β, Wnt, EGF, VEGF, HGF, fibroblast growth factor (FGF), and the like) and the cell alters the repertoire of secreted factors after contacting the one or more factors. The hydrogel matrix is then "loaded" or "primed" with the factors subsequently released by the cell.

In some embodiments, a hydrogel matrix or hydrogel polymer can be "loaded" or "primed" by contacting a factor release molecule with conditioned medium (i.e., liquid culture media collected from factor-secreting cells) such that it is not necessary to culture cells on a hydrogel matrix in order to "prime" or "load" the factor release molecules with cell-secreted factors.

In certain embodiments, the cell adhesion moiety and the factor release molecule are conjugated to the same hydrogel polymer in the hydrogel cell matrix. In other embodiments, the cell adhesion moiety and the factor release molecule are conjugated to different hydrogel polymers in the hydrogel cell matrix.

In certain embodiments, the hydrogel polymers of the hydrogel cell matrix provided herein are linked to each other by a cross-linker polymer. In certain embodiments, the hydrogel polymers of the hydrogel cell matrix provided herein are linked to each other by a cross-linker peptide. In certain embodiments, the hydrogel polymer is linked to one another with a proteolytically cleavable cross-linker polypeptide. See, e.g., Kim and Healy (2003) Biomacromolecules 4:1214. Such proteolytically cleavable cross-linker polypeptides allow for the remodeling of the hydrogel cell matrix. Examples of proteolytically cleavable cross-linker polypeptides can be or include, but are not limited to, a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue) (SEQ ID NO:20), e.g., Pro-X-X-Hy-(Ser/Thr) (SEQ ID NO:21), e.g., Pro-Leu/Gln-Gly-Met-Thr-Ser (SEQ ID NO:22) or Pro-Leu/Gln-Gly-Met-Thr (SEQ ID NO:23). Another example of a protease cleavage site is a plasminogen activator cleavage site, e.g., a uPA or a tissue plasminogen activator (tPA) cleavage site. Specific examples of cleavage sequences of uPA and tPA include sequences comprising Val-Gly-Arg. Another example is a thrombin cleavage site, e.g., CGLVPAGSGP (SEQ ID NO:24). Additional suitable linkers comprising protease cleavage sites include linkers comprising one or more of the following amino acid sequences: 1) SLLKSRMVPNFN (SEQ ID NO:25) or SLLIARRMPNFN (SEQ ID NO:26), cleaved by cathepsin B; SKLVQASASGVN (SEQ ID NO:27) or SSYLKASDAPDN (SEQ ID NO:28), cleaved by an Epstein-Ban virus protease; RPKPQQFFGLMN (SEQ ID NO:29) cleaved by MMP-3 (stromelysin); SLRPLAL-WRSFN (SEQ ID NO:30) cleaved by MMP-7 (matrilysin); SPQGIAGQRNFN (SEQ ID NO:31) cleaved by MMP-9; DVDERDVRGFASFL (SEQ ID NO:32) cleaved by a thermolysin-like MMP; SLPLGLWAPNFN (SEQ ID NO:33) cleaved by matrix metalloproteinase 2 (MMP-2); SLLI-FRSWANFN (SEQ ID NO:34) cleaved by cathespin L; SGVVIATVIVIT (SEQ ID NO:35) cleaved by cathespin D; SLGPQGIWGQFN (SEQ ID NO:36) cleaved by matrix metalloproteinase 1 (MMP-1); KKSPGRVVGGSV (SEQ ID NO:37) cleaved by urokinase-type plasminogen activator; PQGLLGAPGILG (SEQ ID NO:38) cleaved by membrane type 1 matrixmetalloproteinase (MT-MMP); HGPEGLRVGFYESDVMGRGHARLVHVEEPHT (SEQ ID NO:39) cleaved by stromelysin 3 (or MMP-11), thermolysin, fibroblast collagenase and stromelysin-1; GPQGLAGQRGIV (SEQ ID NO:40) cleaved by matrix metalloproteinase 13 (collagenase-3); GGSGQRGRKALE (SEQ ID NO:41) cleaved by tissue-type plasminogen activator (tPA); SLSALLSSDIFN (SEQ ID NO:42) cleaved by human prostate-specific antigen; SLPRFKIIGGFN (SEQ ID NO:43) cleaved by kallikrein (hK3); SLLGIAVPGNFN (SEQ ID NO:44) cleaved by neutrophil elastase; and FFKNIVTPRTPP (SEQ ID NO:45) cleaved by calpain (calcium activated neutral protease).; and CQPQGLAKC (SEQ ID NO:46) cleaved by matrix metalloproteinase 13. In specific embodiments, the proteolytically cleavable cross-linker polypeptide can be cleaved by a matrix metalloproteinase (MMP). In specific embodiments, the proteolytically cleavable cross-linker polypeptide can be cleaved by MMP-13. In specific embodiments, the proteolytically cleavable cross-linker polypeptide includes the amino acid sequence CQPQGLAKC (SEQ ID NO:46).

In another aspect, provided herein is a hydrogel cell matrix system, comprising any one of the hydrogel cell matrices provided herein and a stem cell or progenitor cell encapsulated in the matrix.

Stem Cells

Any suitable stem cell can be used in the hydrogel cell matrix system provided herein. As used herein, the term "stem cell" refers to an undifferentiated cell that can be induced to proliferate. The stem cell is capable of self-maintenance, meaning that with each cell division, one daughter cell will also be a stem cell. Stem cells can be obtained from embryonic, post-natal, juvenile or adult tissue. Stem cells include totipotent stem cells, pluripotent stem cells, and multipotent stem cells. Suitable stem cells include induced pluripotent stem cells.

Stem cells include, e.g., hematopoietic stem cells, embryonic stem cells (e.g., pre-implantation, post-implantation, etc.), mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, induced pluripotent stem cells; and the like; as well as differentiated cells that can be cultured in vitro and used in a therapeutic regimen, where such cells include, but are not limited to, keratinocytes, adipocytes, cardiomyocytes, neurons, osteoblasts, pancreatic islet cells, retinal cells, and the like. The cell that is used will depend in part on the nature of the disorder or condition to be treated.

Suitable human embryonic stem (ES) cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

Suitable human ES cell lines can be positive for one, two, three, four, five, six, or all seven of the following markers:

stage-specific embryonic antigen-3 (SSEA-3); SSEA-4; TRA 1-60; TRA 1-81; Oct-4; GCTM-2; and alkaline phosphatase.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

In yet other embodiments, the stem cell is an induced pluripotent stem (iPS) cell. An induced pluripotent stem (iPS) cell is a pluripotent stem cell induced from a somatic cell, e.g., a differentiated somatic cell. iPS cells are capable of self-renewal and differentiation into cell fate-committed stem cells, including neural stem cells, as well as various types of mature cells.

iPS cells can be generated from somatic cells, including skin fibroblasts, using, e.g., known methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. Methods of generating iPS are known in the art, and any such method can be used to generate iPS. See, e.g., Takahashi and Yamanaka (2006) Cell 126:663-676; Yamanaka et. al. (2007) Nature 448:313-7; Wernig et. al. (2007) Nature 448:318-24; Maherali (2007) Cell Stem Cell 1:55-70; Nakagawa et al. (2008) Nat. Biotechnol. 26:101; Takahashi et al. (2007) Cell 131:861; Takahashi et al. (2007) Nat. Protoc. 2:3081; and Okita et al. (2007 Nature 448:313.

iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28.

Progenitor Cells

In another embodiment, the hydrogel cell matrix system includes a progenitor cell encapsulated by a hydrogel cell matrix. The term "progenitor cell", as used herein, refers to an undifferentiated cell derived from a stem cell, and is not itself a stem cell. Some progenitor cells can produce progeny that are capable of differentiating into more than one cell type. Suitable progenitor cells include, e.g., cardiac progenitors. Any suitable progenitor cell can be used in the hydrogel cell matrix system provided herein. In certain embodiments, the progenitor cell is a cardiac progenitor cell (CPC).

In specific embodiments, the progenitor cell is a progenitor of a cardiomyocyte. Cardiomyocytes express one or more cardiomyocyte-specific markers, where cardiomyocyte-specific markers include, but are not limited to, cardiac troponin I, cardiac troponin-C, tropomyosin, caveolin-3, myosin heavy chain, myosin light chain-2a, myosin light chain-2v, ryanodine receptor, sarcomeric α-actinin, Nkx2.5, connexin 43, and atrial natriuretic factor. Induced cardiomyocytes can also exhibit sarcomeric structures. Induced cardiomyocytes exhibit increased expression of cardiomyocyte-specific genes ACTC1 (cardiac α-actin), ACTN2 (actinin a2), MYH6 (α-myosin heavy chain), RYR2 (ryanodine receptor 2), MYL2 (myosin regulatory light chain 2, ventricular isoform), MYL7 (myosin regulatory light chain, atrial isoform), TNNT2 (troponin T type 2, cardiac), and NPPA (natriuretic peptide precursor type A), PLN (phospholamban). Expression of fibroblasts markers such as Colla2 (collagen 1a2) is downregulated in induced cardiomyocytes, compared to fibroblasts from which the iCM is derived.

In other embodiments, the progenitor cell is a scleral fibroblast.

Methods

In another aspect, provided herein is a method of making a hydrogel cell matrix comprising the step of conjugating a cell adhesion peptide to a first hydrogel polymer; conjugating a factor release molecule to a second hydrogel polymer; and conjugating the first hydrogel polymer to the second hydrogel polymer using a cross-linker polymer, e.g., a cross-linker peptide, such as a proteolytically-cleavable cross-linker peptide. For example, provided herein is a method of making a hydrogel cell matrix comprising the step of conjugating a cell adhesion peptide to a first hydrogel polymer; conjugating a factor release molecule to a second hydrogel polymer; and conjugating the first hydrogel polymer to the second hydrogel polymer using a proteolytically cleavable cross-linker peptide.

In some embodiments, the methods comprise contacting the factor release molecules (e.g., factor release molecules conjugated to hydrogel polymers) with one or more factors (e.g., growth factors), where the one or more factors non-covalently bind to the factor release molecules. This produces a factor contacted (e.g., a growth factor contacted) hydrogel cell matrix. In some embodiments, the methods comprise culturing a cell on a hydrogel cell matrix for any convenient amount of time (e.g., 5 minutes to 2 weeks, e.g., 5-30 minutes, 5 minutes, 10 minutes, 15 minutes, 20 minutes, 30 minutes, 30 minutes to 1 hour, 1 hour, 1-2 hours, 2 hours, 1-3 hours, 3 hours, 2-4 hours, 4 hours, hours, 5 hours, 4-6 hours, 6 hours, 8 hours, 10 hours, 12-24 hours, 12 hours, 18 hours, 24 hours, 24-36 hours, 36 hours, 36-48, 48 hours, 2 days-1 week, 2 days, 3 days, 4 days, 5 days, 6 days, 1 week, 1-2 weeks, or 2 weeks) in any desired condition. Cells secrete many known and/or unknown factors, and the factors secreted by a cell (i.e., cell-secreted factors) will non-covalently bind to the factor release molecules of the hydrogel matrix (or factor release molecules conjugated to a hydrogel polymer). Thus, in some embodiments, a cell is cultured on a subject hydrogel matrix (or in the presence of hydrogel polymers that are conjugated to factor release molecules) to "prime" or "load" the factor release molecules with cell-secreted factors. Those cell-secreted factors can then be subsequently released or presented by the factor release molecules. In some embodiments, the cell-secreted factors are known. In some embodiments, the cell-secreted factors are unknown. In some embodiments, the cell-secreted factors are a mixture of known and unknown factors.

In some embodiments, a cell is cultured on a hydrogel matrix comprising factor release molecules non-covalently bound to one or more known factor(s) (e.g., a growth factor, e.g., TGF-β, Wnt, EGF, VEGF, HGF, FGF, and the like) and the cell alters its repertoire of secreted factors after contacting the one or more factors that are bound to the factor release molecules. The cell-secreted factors then bind to factor release molecules and the hydrogel matrix can thus be said to be "loaded" or "primed" with cell-secreted factors. In some cases, the growth factor is one or more of transforming growth factor-β (TGF-β), vascular endothelial growth factor (VEGF), bone morphogenic protein-2 (BMP2), sonic hedgehog polypeptide (SHH), and fibroblast growth factor 21. (FGF21)

In some embodiments, a hydrogel matrix or hydrogel polymer can be "loaded" or "primed" by contacting a factor release molecule with conditioned medium (i.e., liquid culture media collected from factor-secreting cells). Therefore, it is not necessary to culture cells on a hydrogel matrix in order to "prime" or "load" the factor release molecules with cell-secreted factors.

In another aspect, provided herein is a method of differentiating a stem cell or progenitor cell in a mammalian subject, the method comprising the step of introducing a hydrogel cell matrix of the present disclosure into the mammalian subject. In certain embodiments, the progenitor cell is a cardiac progenitor cell. In other embodiments, the progenitor cell is a scleral fibroblast.

In another aspect, provided herein is a method of introducing a hydrogel cell matrix into a mammalian subject. Because the subject hydrogels have a reasonable working time (e.g., 5-10 minutes) prior to gelation the material can be injected through an 18-28-gauge needle, which facilitates implantation. A subject hydrogels, prior to gelation, can be injected into a mammalian subject in any convenient location, depending on the desired outcome. As a non-limiting example, an acellular or cell-containing formulation of a subject hydrogel cell can be used in the treatment of deep pressure cutaneous wounds or volumetric muscle tissue injury, and the hydrogel can be injected at the wound site, in some cases subcutaneously.

As another non-limiting example, in order to treat diabetes or obesity, a subject hydrogel can comprise a growth factor (or combination of growth factors) that promotes the function of brown adipose tissue and the hydrogel can be injected into existing fat pads. As another non-limiting example, in order to treat diabetes or obesity, a subject hydrogel can comprise a brown adipose cell, a brown adipose stem cell, or a brown adipose progenitor cell, and the hydrogel can be injected into an existing fat pad.

As another non-limiting example, in order to treat severe myopia, a subject hydrogel can comprise a factor or factors that can recruit scleral fibroblasts into the hydrogel matrix, and the hydrogel can be injected in the posterior region of the eye, thereby providing the eye with mechanical support for the maintenance of shape. As another non-limiting example, in order to repair cardiac tissue following myocardial infarction, a subject hydrogel can comprise a factor or factors (and/or an appropriate combination of peptide concentration and matrix stiffness) that can promote the proliferation and differentiation of cardiac progenitor cells, and the hydrogel can be injected into a damaged region of the heart. As another non-limiting example, in order to repair cardiac tissue following myocardial infarction, a subject hydrogel can comprise a cardiac progenitor cell, and the hydrogel can be injected into a damaged region of the heart.

Mammalian subjects include, but are not limited to, rodents (e.g., rats; mice); canines; ungulates (bovines; caprines; ovines; etc.); felines; lagomorphs (e.g., rabbits); non-human primates; and humans. In some embodiments, the subject is a human.

Utility

The system described herein is a system for generating bioactive hydrogel cell matrices with a range of material features that are enabling as a matrix to support cell survival, proliferation and functional ability, as summarized below:

Bioactive: Hyaluronic acid (HyA) is a major component of the ECM of many soft connective tissues, and, thus, is inherently biodegradable, biocompatible, and nonimmunogenic. HyA can direct various cell function like cell migration, proliferation, wound healing by interacting the CD44, Hyaluronan-mediated motility (RHAMM) cell surface receptors.

Combinatorial Synthesis: The hydrogel cell matrix is synthesized from a system of modular components, and the proportions of each component are independently variable to generate hydrogel cell matrices with the desired biological and mechanical properties. Additional components can also be added or removed to generate hydrogel cell matrices with different combinations of bioactive elements. Biological properties can be changed by varying the relative ratio of HyA precursors and mechanical properties can be controlled by changing the weight percentage and crosslinker.

Cell Supportive: The composition of the hydrogel cell matrices also allows for seeding a cellular component directly into the hydrogel during synthesis, and it does not generate any cytotoxic by products as it degrades.

High molecular weight of HyA: The combinatorial method of HyA gel synthesis is enabled through the use of HyA polymers that have been functionalized with a reactive acryl group. A novel method of acrylate HyA (AcHyA) that maintains a higher molecular weight relative to previously published methods has been devised. Use of this high MW AcHyA provides greater control over the hydrogel mechanical properties, and the hydrogels exhibit greater stability in situ.

Prolonged retention of growth factors: The release kinetics of growth factor release from the HyA hydrogel system can be tuned, and growth factors will be retained in the materials for up to 21 days.

Controlled degradation kinetic: The in vivo degradation rate of the hydrogel can be controlled by careful selection of peptide crosslinkers that are sensitive to specific proteolytic crosslinkers that are anticipated in the environment of the implant.

Injectable: HyA hydrogel has a 5-10 minute working time prior to gelation. During this interval, it can be injected through 18-28-gauge needle, which will facilitate cellular implantation.

Physiological: The material used forms a gel using the Michael Addition reaction which occurs at physiological pH, temperatures, and divalent cation concentrations. It also produces no cytotoxic by-products.

Example Uses of a Subject AcHyA Hydrogel:

1) Cardiac Tissue Engineering:

As a specific embodiment of the present disclosure, the hyaluronic acid (HyA) hydrogel parameters can be adjusted to promote myocardial regeneration. This hydrogel contains peptide sequences for cell attachment via binding of integrin receptors, heparin to sequester endogenously synthesized growth factors, and enzymatically degradable matrix metalloproteinase (MMP-13) sensitive peptide crosslinks. The cell adhesive peptide sequences that provide optimal cell adhesion have been determined, and a combination of peptide concentration and matrix stiffness to promote the proliferation and differentiation of cardiac progenitor cells in vitro and in vivo have also been determined. This material can be used as a carrier for stem cells during stem cell therapy to repair cardiac tissue following myocardial infarction.

2) Reinforcement of Scleral Tissue:

As a second exemplary embodiment, HyA hydrogel parameters have been determined that can be used to support scleral tissue in patients with severe myopia. This scaffold contains peptides to promote cell adhesion and conjugated heparin that releases protein growth factors at a controlled rate. This material can be injected in the posterior region of the eye, and will recruit local, scleral fibroblasts into the matrix and encourages them to remodel the material, thus providing mechanical support to the eye for maintenance of its shape.

3) Fat Tissue Engineering:

As a third embodiment, HyA hydrogel parameters have been developed that promote the survival and differentiation of brown adipose tissue cells in vivo. Brown adipose cells are a highly specialized cell type with specific physiological functions to accelerate the body's metabolism and to generate body heat. While maintenance of this phenotype is difficult to achieve in vivo, a specific ratio of cell adhesion peptides that promote the function of brown adipose cells has been identified. A synthetic brown adipose tissue has been produced that can be injected into existing fat pads as a treatment for obesity and type 2 diabetes.

4) Wound Healing Matrix:

An acellular formulation of the HyA gels can be used as a void filler in the treatment of deep pressure cutaneous wounds and volumetric muscle tissue injury.

5) Drug Depot:

The HyA gels can be used as a drug depot by taking advantage of their tuneable release kinetics and degradation rate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1: Growth Factor Sequestering and Presenting Hydrogels Promote Survival and Engraftment of Transplanted Stem Cells Materials and Methods HyA Hhydrogel Materials Hyaluronic acid (HyA, sodium salt, 1.0 MDa and 500 kDa) was generously donated by Lifecore Biomedical (Chaska, Minn.). Adipic dihydrazide (ADH), 1-ethyl-3-[3-(dimethylamino)propyl]carbodiimide (EDC), sodium hydroxide (NaOH), hydrochloric acid (HCl) and 1-hydroxybenzotriazole (HOBt) were purchased from Aldrich (Milwaukee, Wis.). Dimethyl sulfoxide (DMSO), N-Acryloxysuccinimide (NAS), acetone, ethanol were obtained from Fisher Scientific (Waltham, Mass.). Paraformaldehyde (16% in $H_2O$) was obtained from Electron Microscopy Sciences (Hartfield, Pa.). Calcein was purchased from BD Biosciences (Pasadena, Calif.). The MMP-degradable crosslinker peptide (CQPQGLAKC; SEQ ID NO:46) and the 15 amino-acid bspRGD(15) adhesion peptide (CGGNGEPRGD-TYRAY; SEQ ID NO:1) were synthesized by American Peptide (Sunnyvale, Calif.). Dialysis membranes (10000 MWCO, SpectraPor Biotech CE) were purchased from Spectrum Laboratories (Rancho Dominguez, Calif.). All chemicals were used as received. All cell culture reagents were purchased from Invitrogen (Carlsbad, Calif.). 1× Dulbecco's phosphate buffered saline (DPBS) was purchased from Invitrogen.

Synthesis of AcHyA Hydrogel Components

Figure 2A:
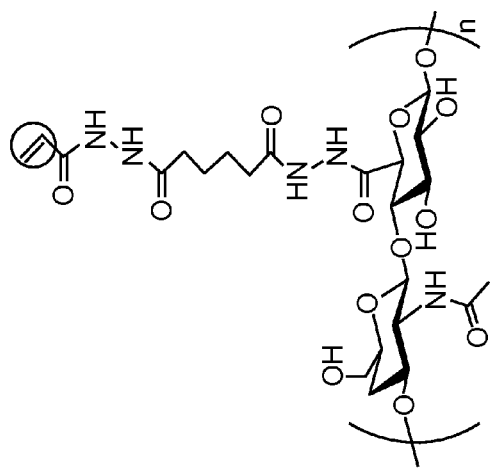
FIG. 2-D depict chemical characteristics and validation of AcHyA components. Proton ($^1$H) NMR spectroscopy demonstrates the acrylate bound to the (A) AcHyA macromers compared to (B) degraded hydrogel and (C) AcHyA-RGD. The (D) dependency on the percentage of TGFβ1 retained by the hydrogel on the weight percentage of incorporated heparin is also depicted as determined by ELISA.
Figure 2B:
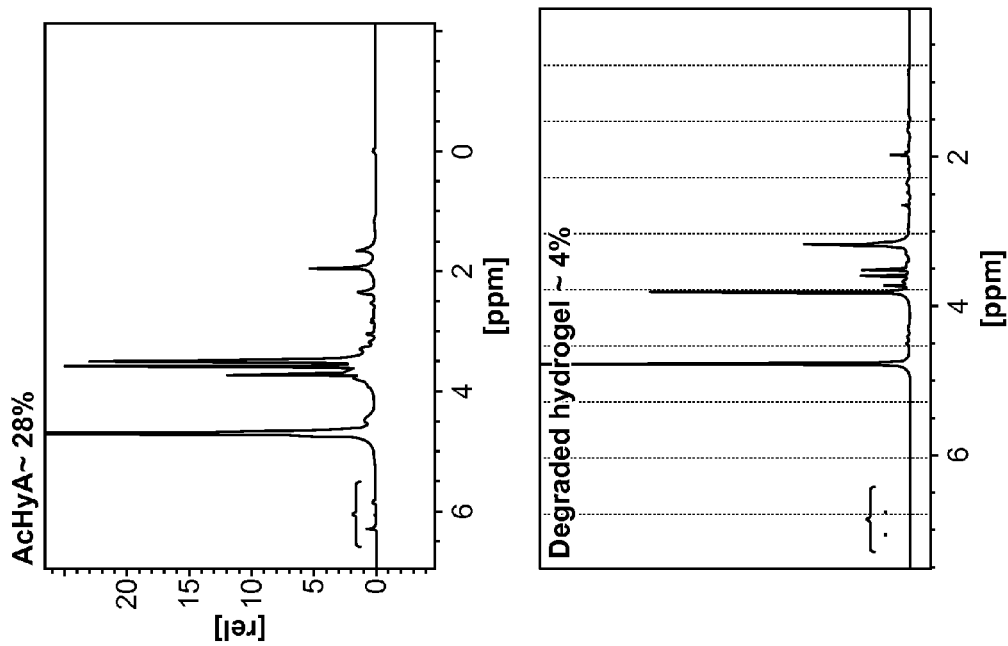
Figure 2C:
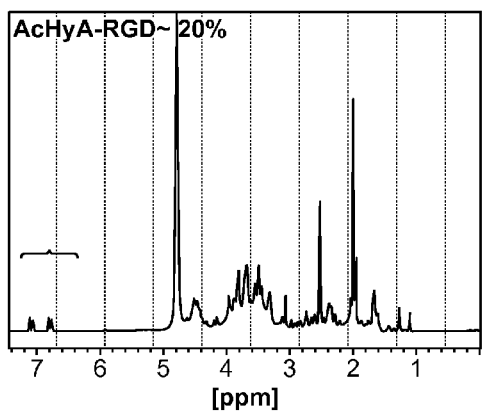

Functionalization of HyA with acrylate groups using a two-step synthesis method and functionalization of heparin with a thiol group were performed as follows (FIG. 1):

1) Acrylation of HyA: A HyA derivative carrying hydrazide groups (HyA-ADH) was synthesized using a previously reported method[43]. Specifically, 30 molar excess of ADH was added to HyA in deionized (DI) water (100 ml, 3 mg/ml). Solution pH was adjusted to 6.8 using 0.1M NaOH and 0.1M HCl. EDC (3 mmol) and HOBt (3 mmol) were dissolved separately in DMSO/water (1/1 volume ratio, 3 ml) and added to the HyA solution sequentially. The solution was allowed to react for 24 hours, and the pH was maintained at 6.8 for at least the first 6 h. After 24 hrs, the solution pH was adjusted to 7.0 and exhaustively dialyzed against DI water. Then, NaCl was added to produce a 5% (w/v) solution, and HyA-ADH was precipitated in 100% ethanol. The precipitate was redissolved in $H_2O$ and dialyzed again to remove the salt. Subsequently, NAS (700 mg) was reacted to the HyA-ADH solution (300 mg, 100 mL DI water) to generate acrylate groups on the HyA)[21]. The product was then lyophilized for 3 days to obtain acrylated HyA (AcHyA). Proton (1H) NMR, using a previously described analysis 3, confirmed that ~28% of the available carboxyl groups were conjugated with acrylate groups on the final acrylated HyA product (AcHyA; FIG. 2a-c).

Figure 2D:
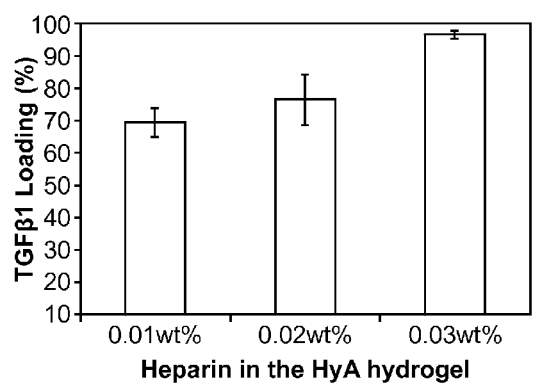

2) Synthesis of Thiolated Heparin (heparin-SH): Heparin-SH synthesis was adapted from a previous report[4]. Heparin (50 mg) was dissolved in DI water at a concentration of 5 mg/mL and reacted with an excess amount of cysteamine in the presence of EDC and HOBt at pH 6.8 for 5 h at room temperature. Next, the reaction solution was exhaustively dialyzed using a dialysis cassette to remove all small molecules not attached to heparin and lyophilized. After that, a 10-fold molar (moles per COOH of heparin) excess of tris(2-carboxyethyl)phosphine (TCEP) was added to reduce the oxidized disulfide groups in order to free thiol groups. This solution was allowed to react for 3 h at pH 7.5 and, then adjusted to pH 5.0 by the addition of 1.0 N HCl. The acidified solution was dialyzed against dilute HCl (pH 5.0) containing 100 mM NaCl, followed by dialysis against dilute HCl at pH 5.0. Then heparin-SH was lyophilized for 3 days, and the percentage of conjugation of thiol groups on the final product (heparin-SH) was determined by colorimetric Ellman assay. TGFβ1 was added to AcHyA-Heparin to associate it with the heparin via a non-covalent, charge-dependent interaction. Retention of exogenous TGFβ1 in the hydrogels was dependent on the weight percentage of the incorporated heparin, and was as high as 98% for 0.03 wt. % gels (FIG. 2D).

Synthesis of HyA Hydrogels

HyA derivative carrying hydrazide groups (HyAADH) were synthesized using previous methods,43 and acryloxy-succinimide (700 mg) was subsequently reacted to the HyAADH solution (300 mg, 100 mL deionized (DI) water) to generate acrylate groups on the HyA (AcHyA). The presence of the acrylate group on AcHyA was confirmed by 1H NMR. The AcHyA-RGD derivative was synthesized by reacting CGGNGEPRGDTYRAY (bsp-RGD (15); SEQ ID NO:1) ( )(10 mg) with AcHyA solution (25 mg, 10 mL DI water) at room temperature. Separately, thiolated-heparin was synthesized by reacting heparin (50 mg, 10 mL DI water) with the excess of cysteamine in the presence of EDC and HOBt at pH 6.8. AcHyA (4 mg), AcHyA-RGD (6 mg), and thiolated heparin (heparin-SH) (0.03 wt %) were dissolved in 0.3 mL of triethanolamine-buffer (TEOA; 0.3 M, pH 8), and incubated for 15 minutes at 37° C. HyA hydrogels were generated by in situ crosslinking of the HyA precursors with the MMP-13-cleavable peptide sequence CQPQGLAKC (SEQ ID NO:46) (50 μL TEOA buffer)[20,29].

Mechanical Characterization of AcHyA Hydrogels

Functionalized AcHyA components were combined at defined ratios, and then in situ crosslinking of the HyA hydrogel was achieved with a 10 residue peptide. Terminal cysteines at each end of the peptide were used to react via Michael-type addition reaction with any available acrylate groups in the AcHyA mixture. Gelation of the hydrogel occurred within 2-10 min, as determined by measuring a time-sweep of its mechanical response to 0.1% strain at 1 Hz using a oscillatory rheometer. Viscoelastic properties of the hydrogel were determined by an oscillatory rheometer with parallel plate geometry (25 mm diameter) under 10% constant strain and frequency ranging from 0.1 Hz to 10 Hz. The viscoelastic properties of the resulting hydrogel were dependent on the weight percentage of AcHyA and the crosslinking density, which was defined as moles of available cysteines on the peptide crosslinker relative to moles of acrylate groups on the AcHyA.

Cell Culture, Cell Viability, Adhesion and Proliferation

The $GFP^+/Sca-1^+/CD105^+/CD45^-$ CPCs were isolated and cultured in Iscove's Modified Dulbecco's Medium (IMDM) basal media containing 10% Fetal bovine serum (FBS) and 1% Penicillin-Streptomycin (PS) as previously described[39]. For cell encapsulation in the HyA hydrogels, confluent cells were trypsinized, collected cells were encapsulated density of $5 \times 10^6$ cells/mL in HyA hydrogel. Before adding the cell culture media, cell-gel constructs were incubated for 30 minutes at 37° C. to allow sufficient crosslinking to occur for gelation. Cell viability in the hydrogel was assessed by a Live/Dead staining kit (Invitrogen), and cell attachment was characterized by F-actin staining. Cell proliferation inside the hydrogels was quantified using the Alamar blue assay[44,45].

In Vivo Implantation Study

To evaluate performance of the HyA hydrogels to promote CPC survival and to direct cell fate in vivo, CPC/hydrogel suspension (100 μL) containing renilla luciferase (rLuc) tranducted CPCs (5 millions cells/mL) was injected into the subcutaneous tissues adjacent to the gastrocnemius muscle of the right hind limb of syngeneic C57BL/6 mice. An equivalent volume of CPC/PBS was transplanted in the left leg of each mouse. In vivo cell proliferation at predetermined time point was assessed on the basis of radiance $(p/s/cm^2/SR)$ of bioluminescence images (BLI) in each of the hind-limb regions of interest. After 12 days, the mice were sacrificed and the hydrogel implants were harvested for Masson's trichrome and CD31 staining.

Results

Figure 3A:
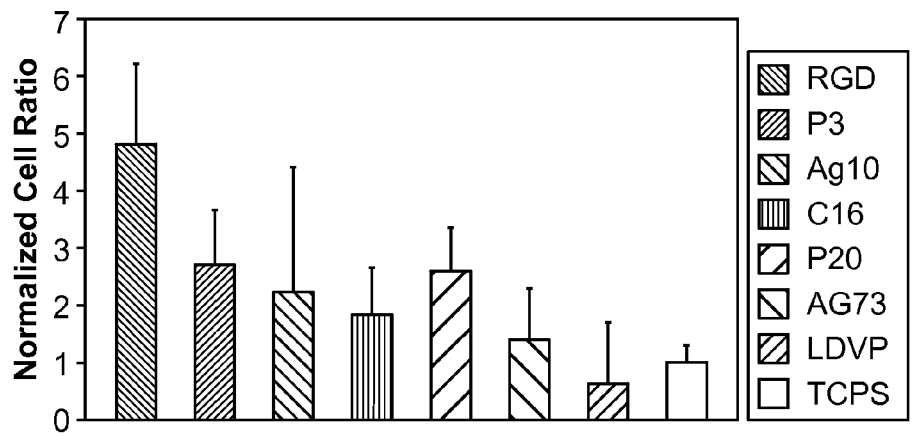
FIGS. 3A-C depict CPC (A) cellular adhesion and (B) proliferation resulting from the use of various adhesion peptides: CGGNGEPRGDTYRAY (bsp-RGD, SEQ ID NO:1), CGGNRWHSIYITRFG (AG-10, SEQ ID NO:9), CGGEILDVPST (LDVP, SEQ ID NO:47), CGGRKRLQVQLSIRT (AG73, SEQ ID NO:11), and CGG-KAFDITYVRLKF (C16, SEQ ID NO:12), RNIAEIIK-DIGC (P20, SEQ ID NO:48), CGGVSWFSRHRYSPFAVS (P3, SEQ ID NO:8). Also depicted is (C) the effect of blocking integrins on cell adhesion to hydrogel using various blocking antibodies.
Figure 3B:
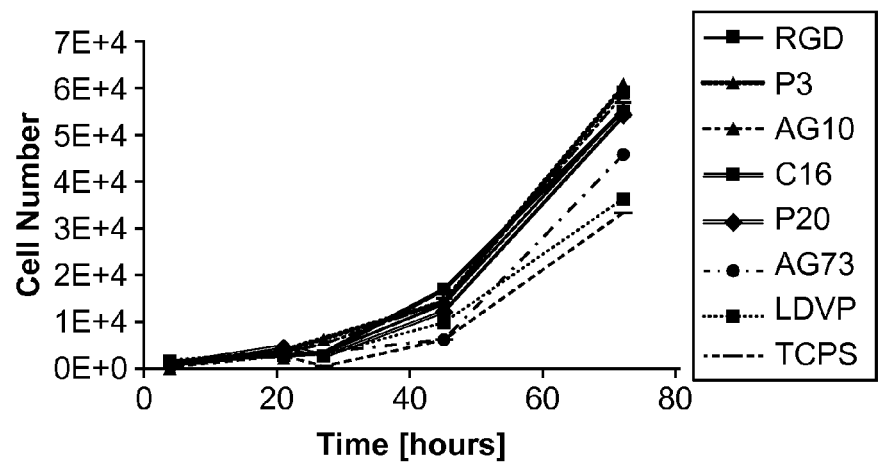
Figure 3C:
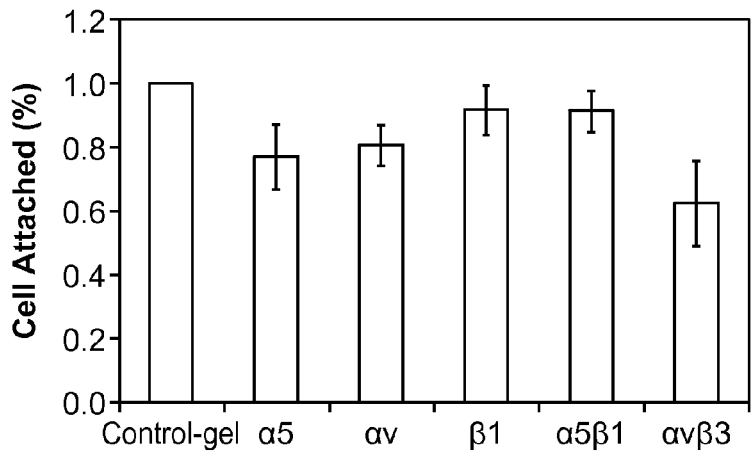
Figure 4A:
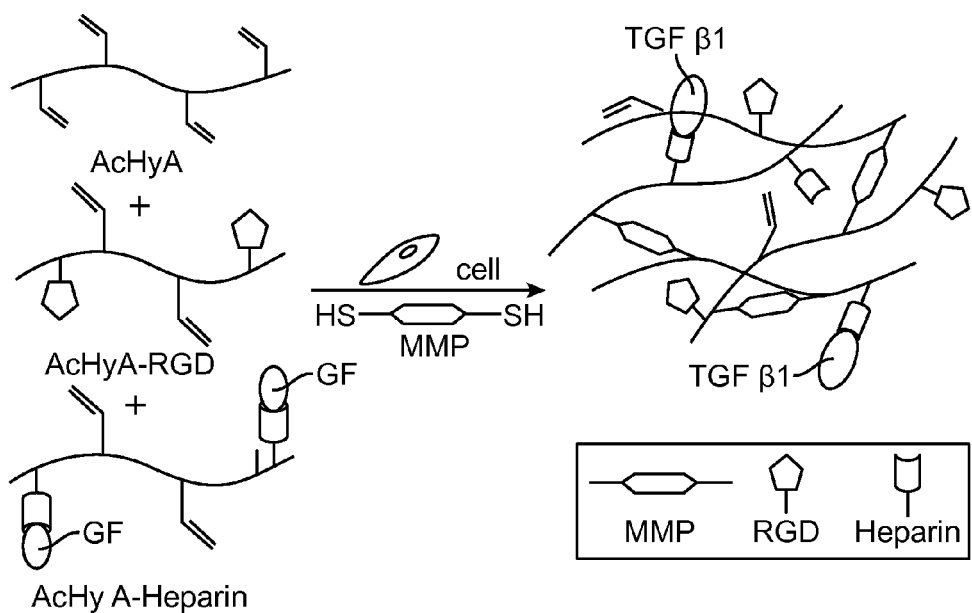
FIGS. 4A-D depict a schematic and method for gel synthesis. (A) HyA hydrogels containing the cell adhesive bspRGD(15) peptide (SEQ ID NO:1) and heparin as a growth factor presenting/releasing agent were synthesized by using (B), bis-cysteine enzymatically-degradable peptide crosslinkers. Also depicted is (C) the time required to initiate gelation and (D) retention of TGFβ1 depending on weight percentage of heparin in the HyA hydrogel.
Figure 4B:
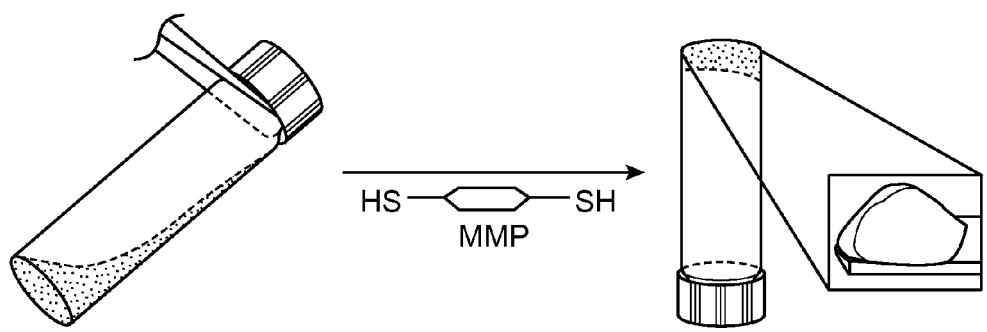
Figure 4C:
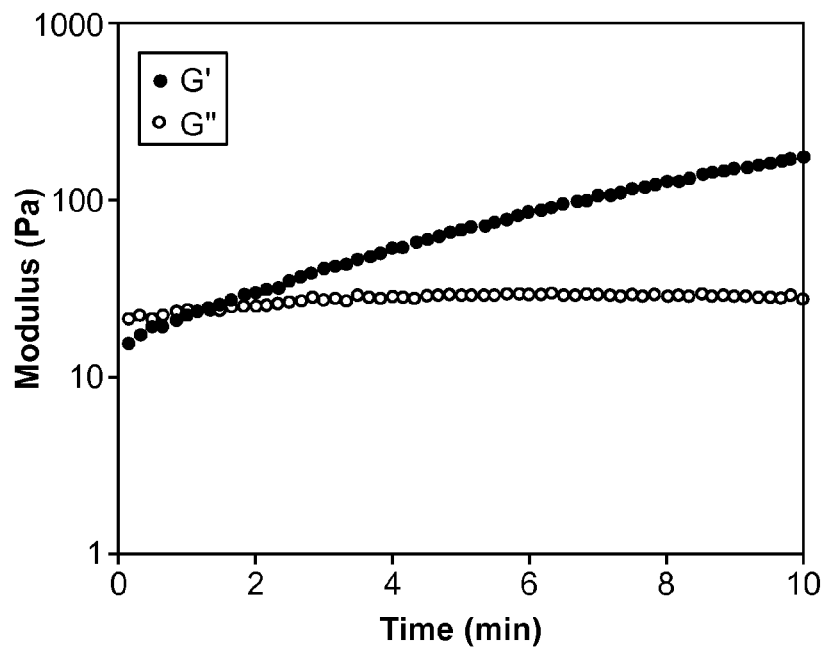

Soluble growth factors have their effect on cells for limited time due their poor stability, soluble presentation, and short-half life time. Therefore, for this study, two discrete hydrogel components were synthesized: AcHyA conjugated with the adhesion peptide bspRGD(15) (AcHyA-RGD)[34] and AcHyA conjugated with the glycosaminoglycan heparin (AcHyA-Heparin). AcHyA and thiolated hepatin (heparin-SH) were synthesized and characterized according to FIG. 1 and FIG. 2. The thiolated heparin macromers were incorporated into the HyA based hydrogel for solid-phase presentation and prolonged retention of growth factors either produced by the entrained cells or added exogenously. The adhesion peptide was chosen based on a screen of seven peptides with known integrin engagement for both adhesion and proliferation (FIG. 3). HyA hydrogels with a range of biochemical and physical parameters (Table 2, below) were made by in situ crosslinking of AcHyA components (AcHyA-RGD, AcHyA-Heparin) via the Michael-type addition reaction with short peptide sequences presenting terminal cysteine residues (FIG. 4A-B).

TABLE 2

| HyA Hydrogel Parameters | Range of values evaluated |
| --- | --- |
| bspRGD(15) peptide density | 120-380 μM |
| crosslinking density peptide density | 25%-100% |
| HyA weight percentage | 1-3 wt % HyA (15-850 Pa) |
| heparin weigh density | 0.01-0.03 wt % |
| TGFβ1 concentration | 40 nM |

Figure 4D:
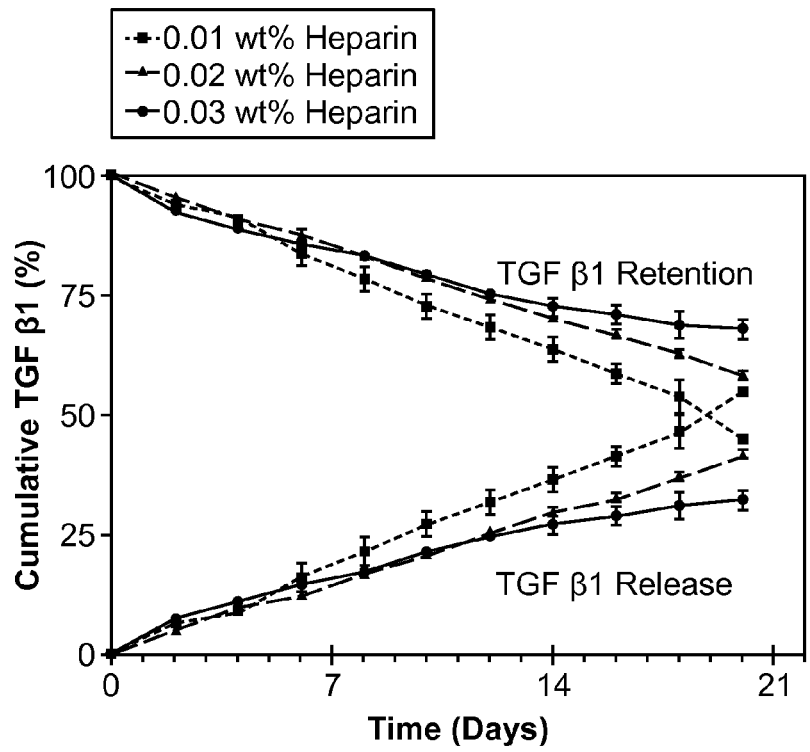
Figure 5A:
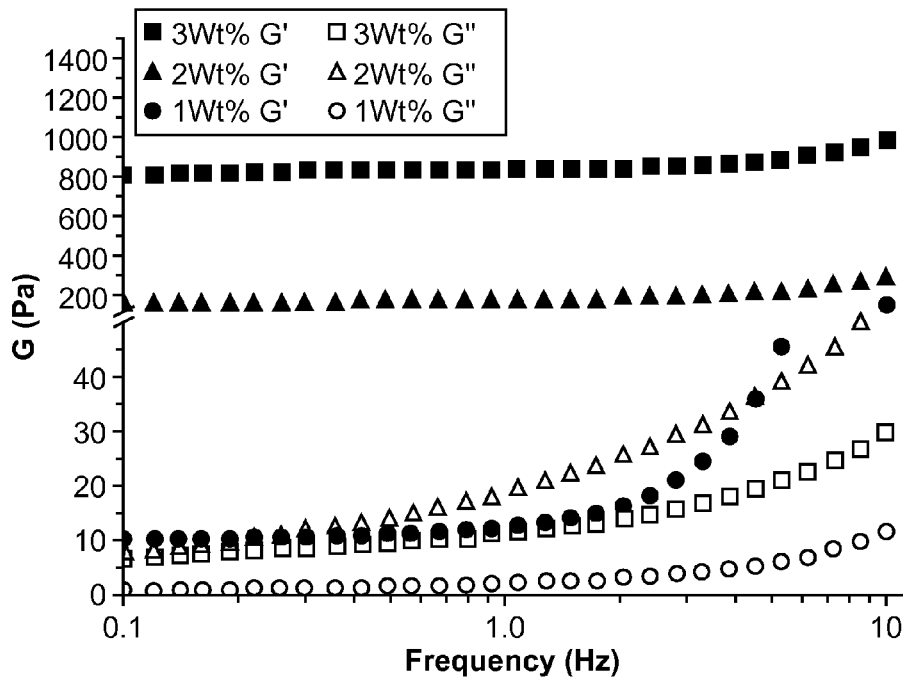
FIGS. 5A-B depict the rheological properties of the hydrogel at (A) various weight percentages HyA and (B) various crosslinking densities, where filled symbol represents the storage modulus, and the open symbol represents the loss modulus.
Figure 5B:
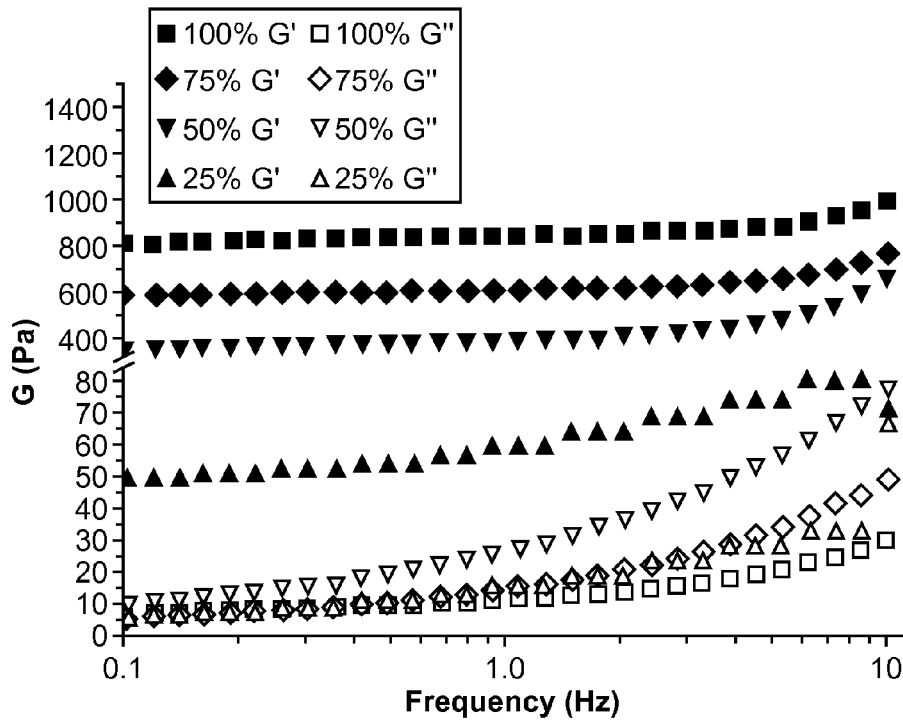

Gelation of the hydrogel was initiated after approximately 60 seconds and was completed within 15 min, as determined by measuring a time-sweep at 0.1% strain and 1 Hz using an oscillatory rheometer (FIG. 1C). The viscoelastic properties of the resulting hydrogel were dependent on both the weight percentage of AcHyA and the crosslinking density, which was defined as the moles of available cysteines on the peptide crosslinker relative to the moles of acrylate groups on the AcHyA (FIG. 5A-B). Exogenous TGFβ1 was used in this study based on previous investigations demonstrating the role of TGFβ1 to promote capillary tube formation by CPCs[35] and endothelial cells[36], and that the endothelial cell surface glycoprotein CD105/endoglin is a coreceptor in the TGFβ1-TGFβR receptor complex with specific involvement in noncanonical cell survival, and vascular development and remodeling[37,38]. Covalent conjugation of heparin (0.03 wt %) in the HyA network retained up to 70% of the TGFβ1, relative to the initial concentration via the protein's heparin-binding domain (FIG. 4D).

Figure 6A:
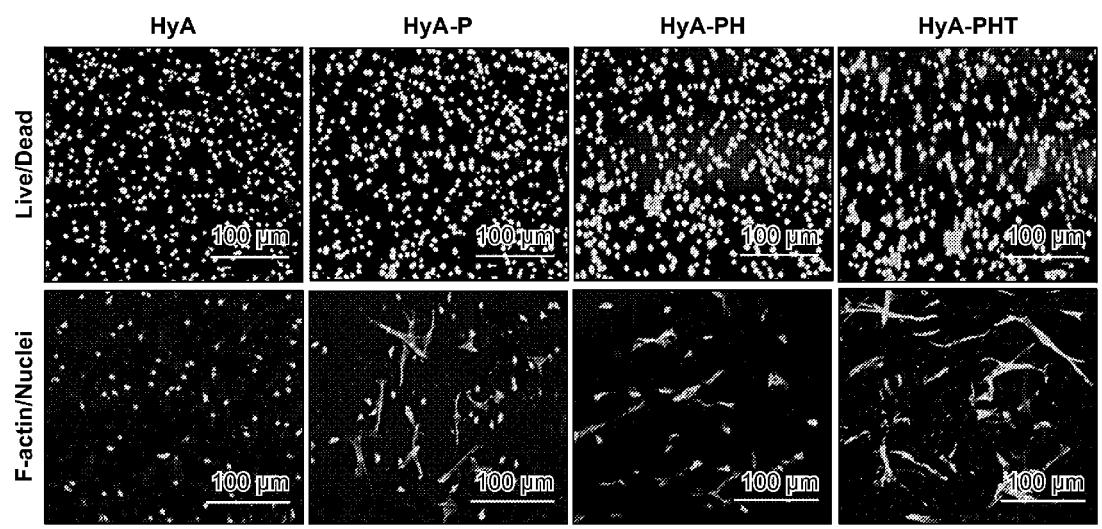
FIGS. 6A-C depict CPC viability, adhesion, and proliferation in HyA hydrogels. (A) Viability, (A) adhesion, (B) spreading, and (C) proliferation were significantly enhanced by the addition of adhesion peptide and TGFβ1.
Figure 6B:
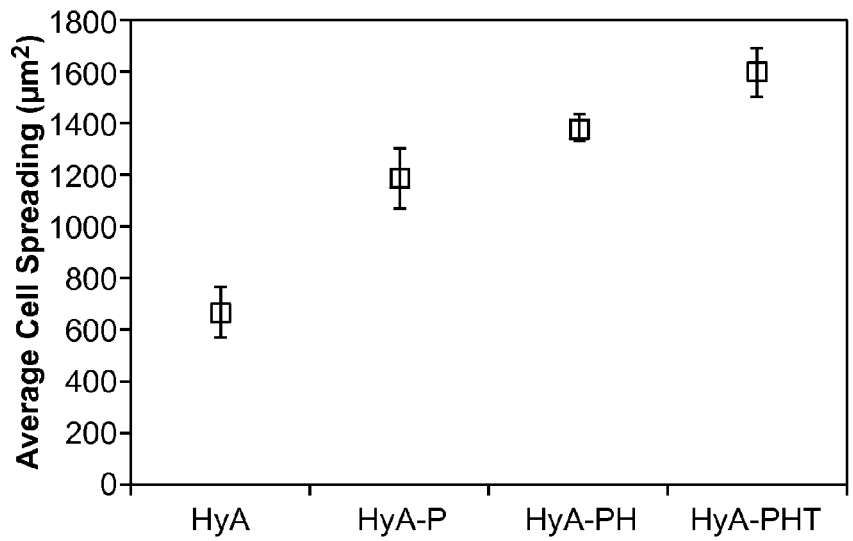
Figure 6C:
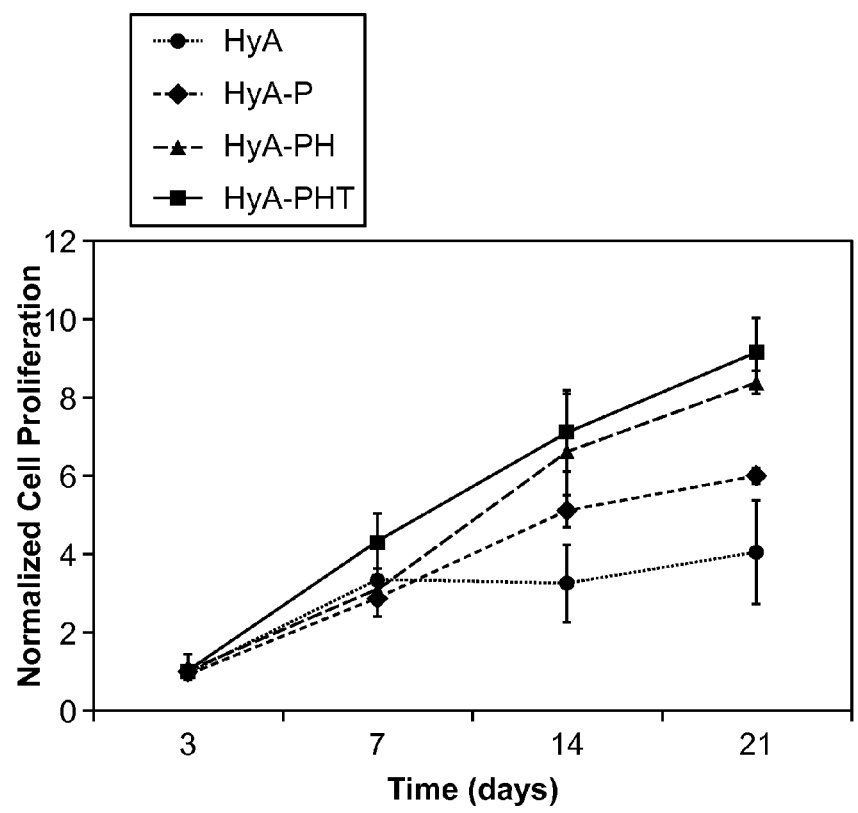
Figure 7A:
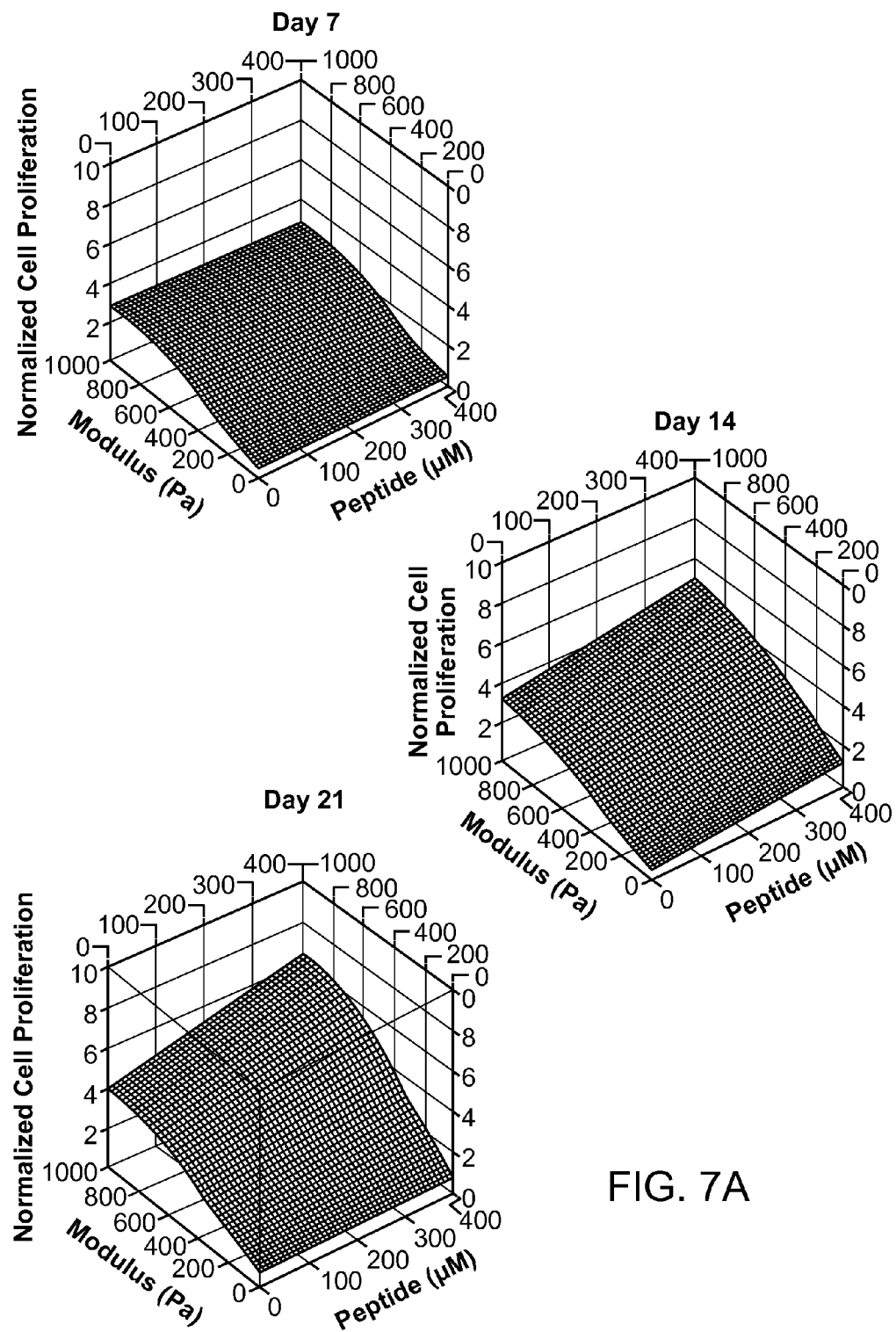
FIGS. 7A-B depict the effects of hydrogel properties on CPC proliferation. Shown are (A) RSM plots of CPC proliferation in HyA-PHT hydrogels containing various weight percentages of HyA precursors and concentrations of the cell adhesive ligand bspRGD(15) and (B) CPC proliferation as a function of HyA-PHT hydrogel stiffness at different bdpRGD(15) (SEQ ID NO:1) densities.
Figure 7B:
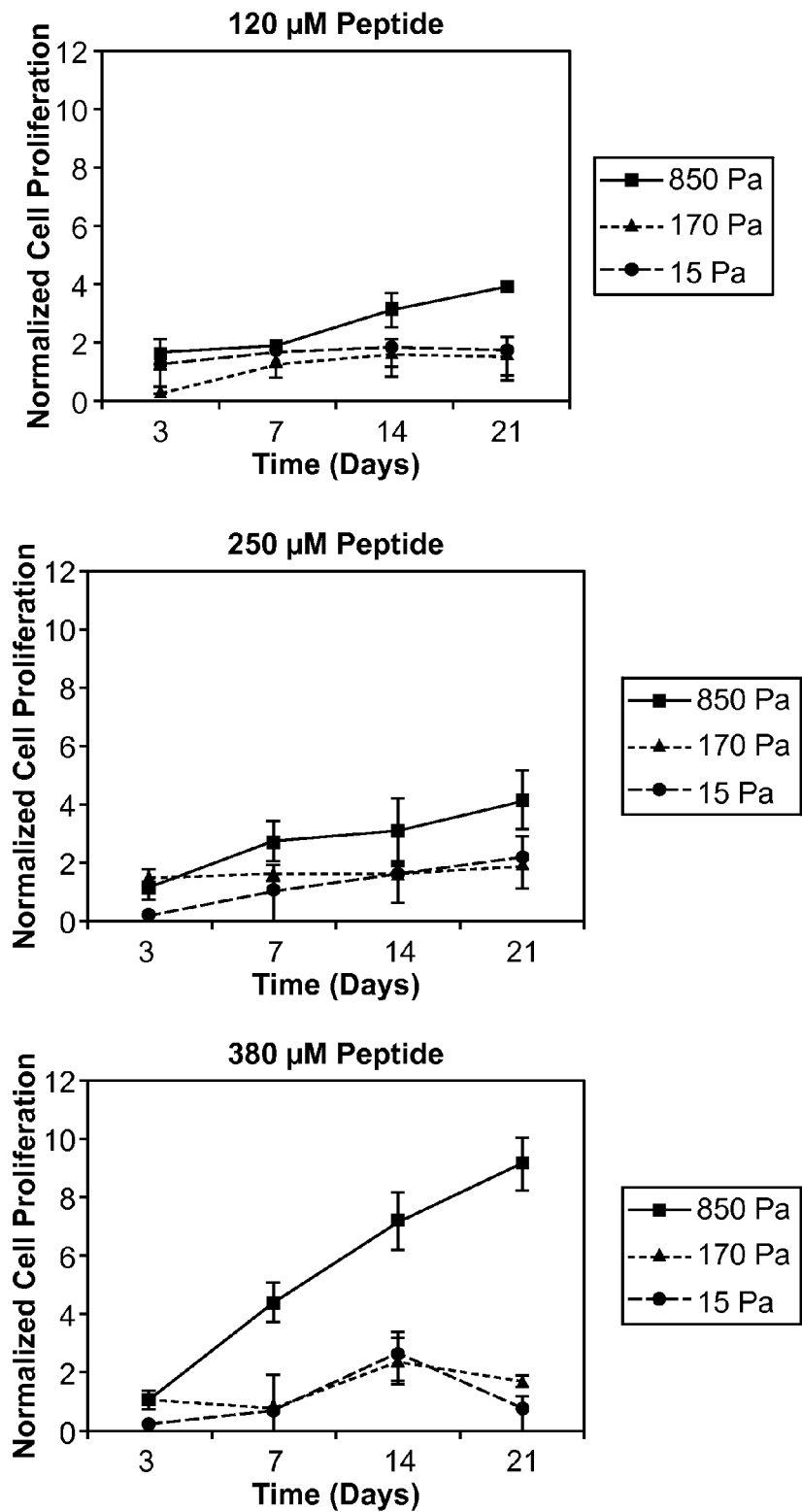
Figure 8:
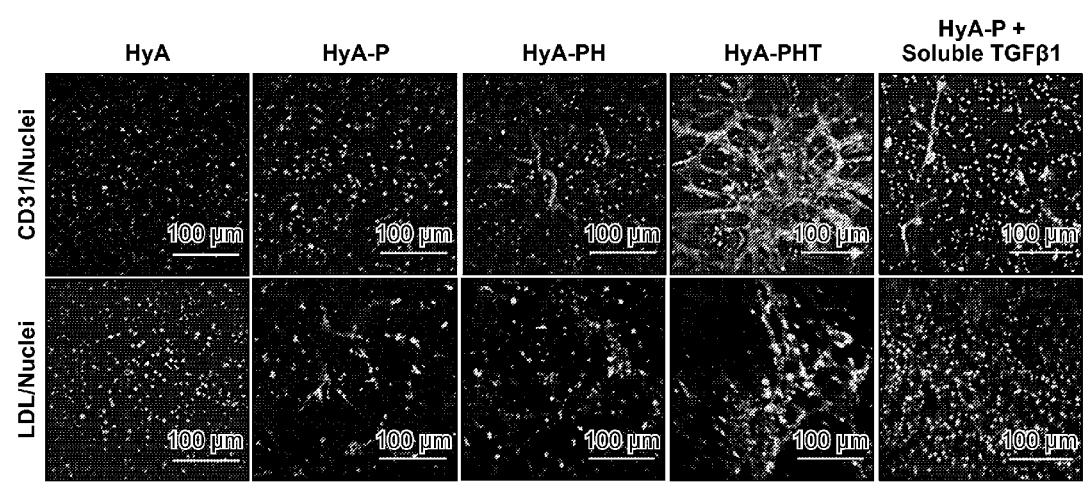
FIG. 8 depicts confocal images of cells cultured 12 days in HyA, HyA-P, HyA-PH and HyA-PHT hydrogel and immunostained for endothelial cell markers CD31 and acetylated low density lipoprotein (Ac-LDL) uptake. HyA-P treated with an equivalent concentration of soluble TGFβ1 as delivered in HyA-PHT is included as a control.

A versatile population of cardiac progenitor cells (CPCs) was used to investigate the role of each hydrogel component on stem cell fate determination. The CPCs are a Sca-1+/CD105+/CD45− population of cells that readily differentiate into cardiomyocytes, smooth muscle, and endothelial cells under the appropriate induction conditions[39]. To evaluate the effect of each AcHyA component on CPC proliferation and differentiation, four combinations of HyA hydrogels were synthesized: (1) AcHyA only (HyA); (2) AcHyA and AcHyA-RGD (HyA-P); (3) AcHyA, AcHyA-RGD and AcHyA-Heparin (HyA-PH); and, (4) AcHyA, AcHyA-RGD and AcHyA-Heparin-TGFβ1 (HyA-PHT). Minimal (<5%) CPC death was observed in each of the hydrogels, independent of the combination of components (FIG. 6A-C). CPCs seeded within all three hydrogels containing AcHyA-RGD exhibited robust spreading and elongated cellular morphology, whereas CPCs seeded in the hydrogel containing only HyA remained rounded and did not assume a typical adherent cell morphology. The effect of bspRGD(15) density and hydrogel stiffness on CPC proliferation was evaluated using response surface methodology (RSM) to analyze the multi-parametric data (FIG. 7A-B). CPC proliferation was linearly dependent on bspRGD(15) density within the evaluated range, whereas the effect of hydrogel stiffness plateaued at approximately 800 Pa. Furthermore, the matrix stiffness had greater influence on the proliferation rate of the CPCs compared to peptide density, as the former appeared to dominate the response surfaces at every time point. Differentiation of Sca-1+/CD45− population of CPCs into endothelial cells within the four hydrogels was measured by immunostaining for CD31 and uptake of acetylated low-density lipoprotein (Ac-LDL) (FIG. 8). Cellular network formation was only observed in HyA-PHT hydrogels, (FIG. 8) which indicated exogenous TGFβ1 presented in the network induced tubule network formation, consistent with previous investigations demonstrating the role of TGFβ1 to promote capillary tube formation by CPCs[35] and endothelial cells[36]. The presentation of the TGFβ1 by heparin substantially facilitates the network formation process, as an equimolar concentration of TGFβ1 supplied as a soluble mediator in HyA-hydrogels lacking heparin was insufficient to generate a similar neovascular response.

Figure 9A:
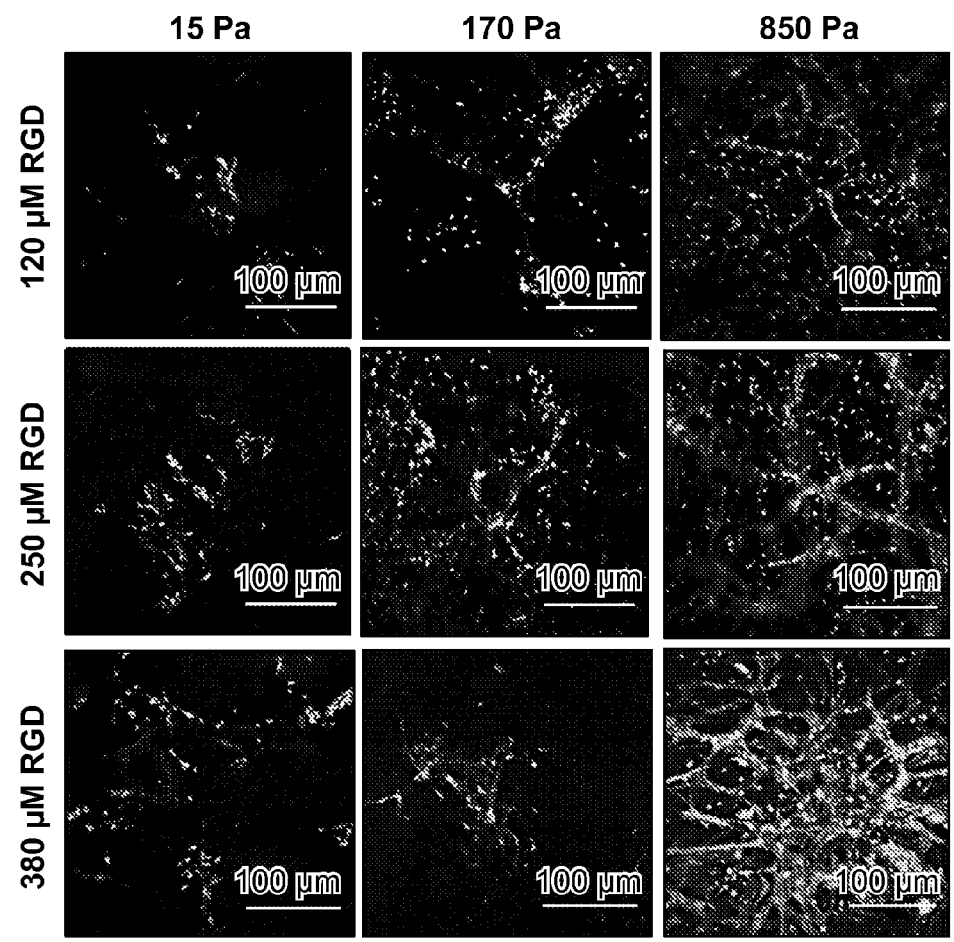
FIGS. 9A-E depict hydrogel culture conditions that promote tube formation by CPCs. Shown is (A) vascular-like tube formation of CD31 positive cells in HyA-PHT hydrogel (B) total tube length and (C) average tube thickness as a function of BSPRGD(15) peptide (SEQ ID NO:1) density and gel modulus. Also depicted is the (D) 3D structure and (E) lumen of a tubular structure formed of CD31 cells.
Figure 9B:
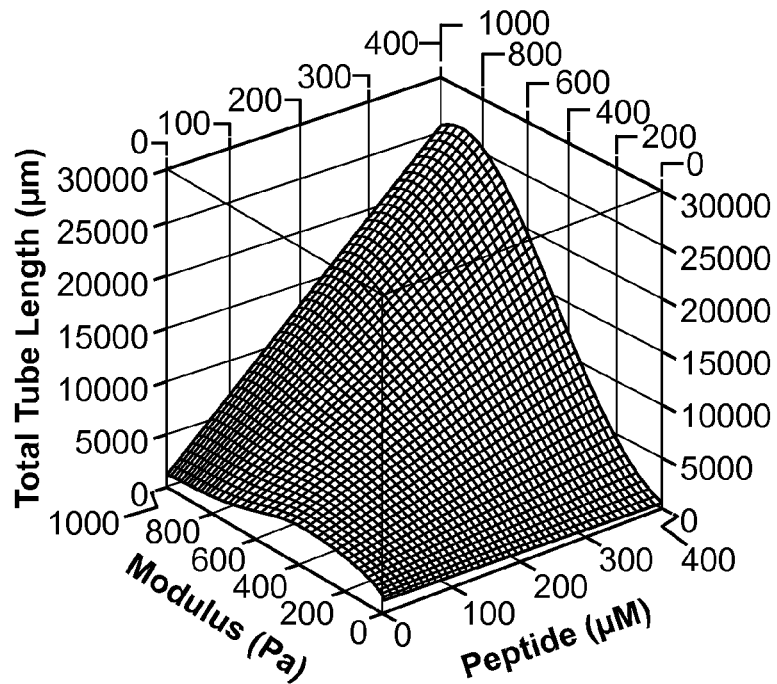
Figure 9C:
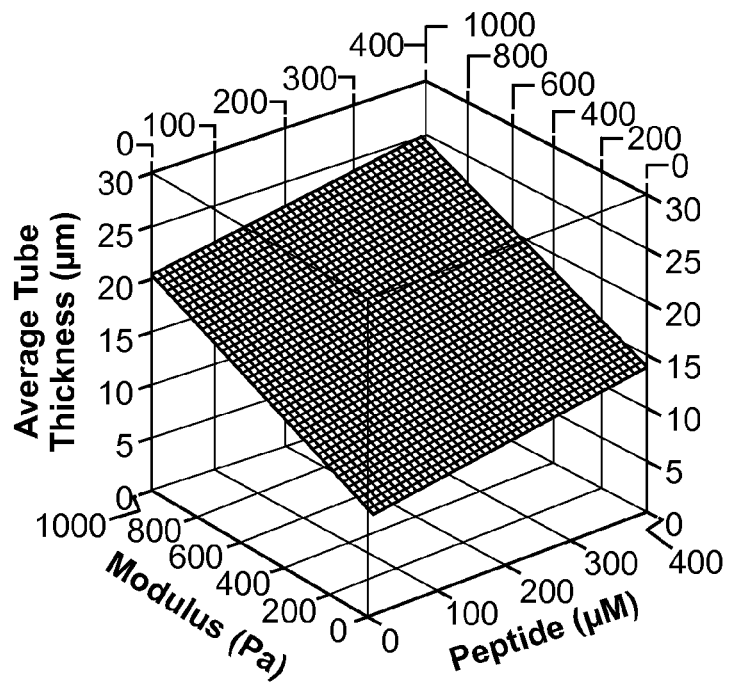
Figure 9D:
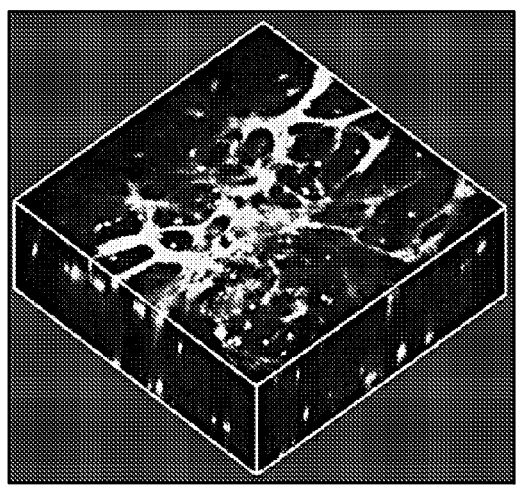
Figure 9E:
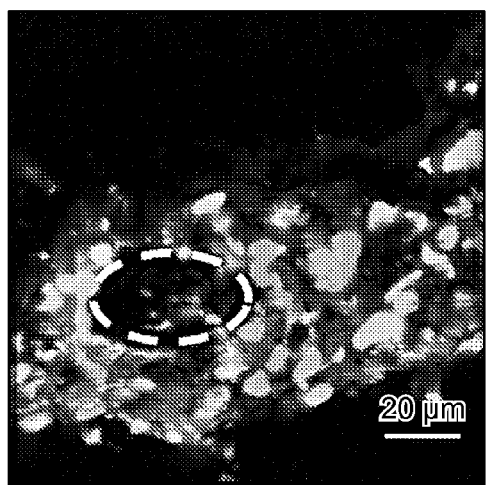

The effect of HyA hydrogel stiffness and bspRGD(15) density on nascent endothelial tube formation was investigated. After culture for 12 days in HyA-PHT hydrogels, formation of tubular networks was dependent on both hydrogel modulus and peptide density (FIG. 9A). Response of total tubule length to the bspRGD(15) peptide density was approximately linear within the range evaluated in this study. Similarly, the thickness of the tubules formed in HyA-PHT hydrogels exhibited a linear response to both hydrogel modulus and bspRGD(15) peptide density, although this tubule characteristic was more sensitive to the matrix stiffness parameter (FIG. 9B-C) These complex three-dimensional networks (FIG. 9D) contained a central lumen (FIG. 9E), suggesting that CPCs in the HyA-PHT hydrogels were capable of forming nascent vessels.

Figure 10A:
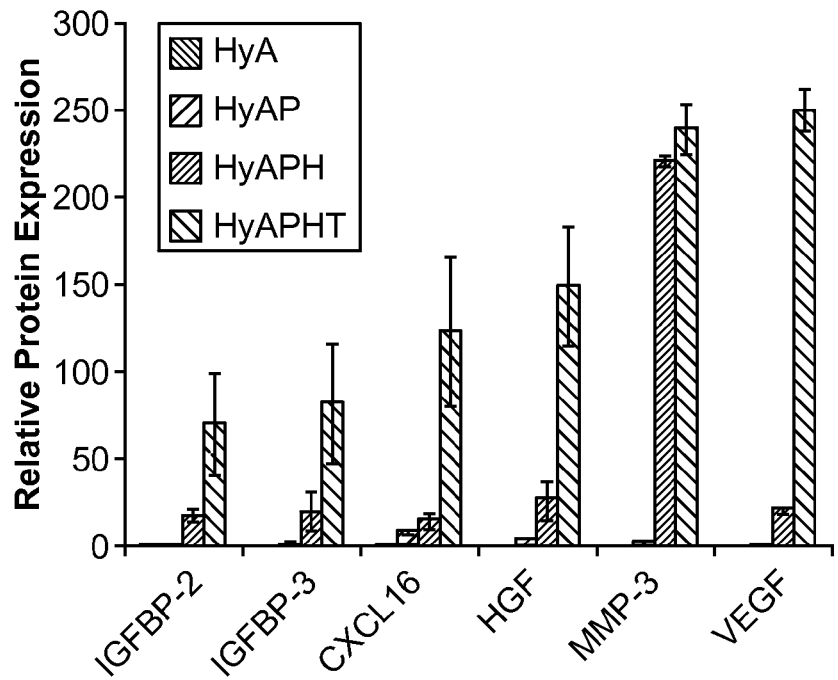
FIGS. 10A-B depict the concentration of secreted angiogenic factors produced by CPCs and sequestered within HyA-PHT hydrogel after 12 days.
Figure 10A:
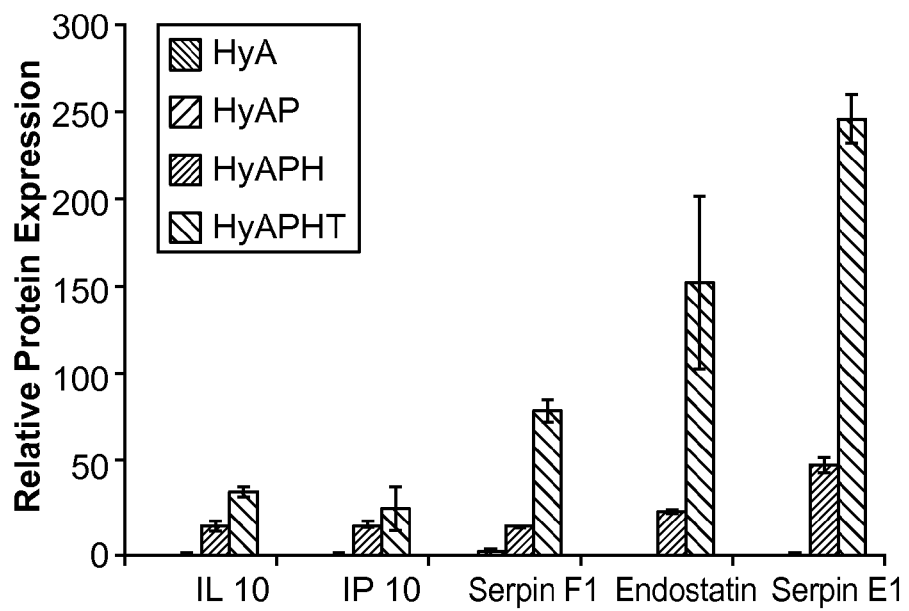
Figure 10B:
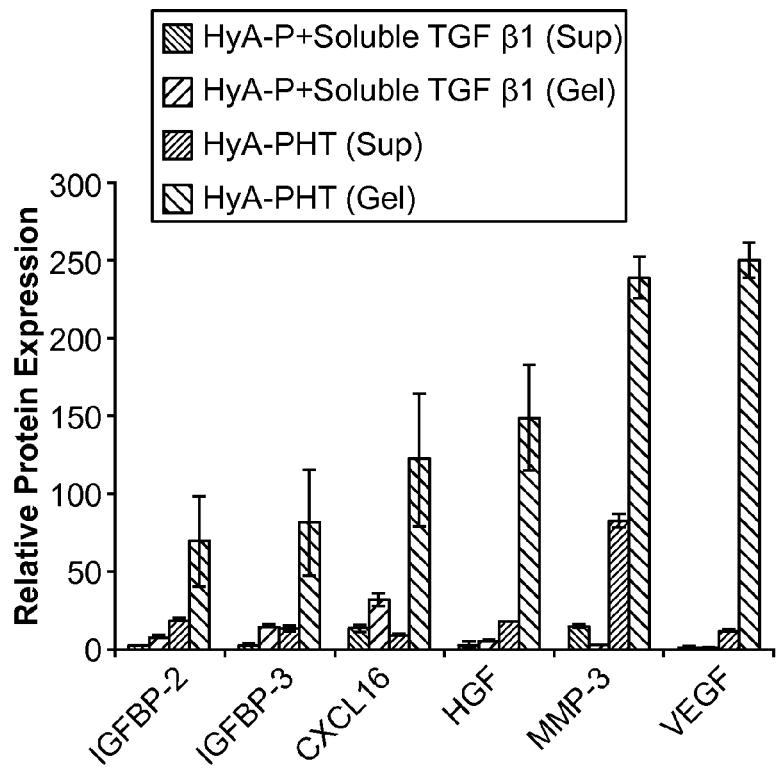
Figure 10B:
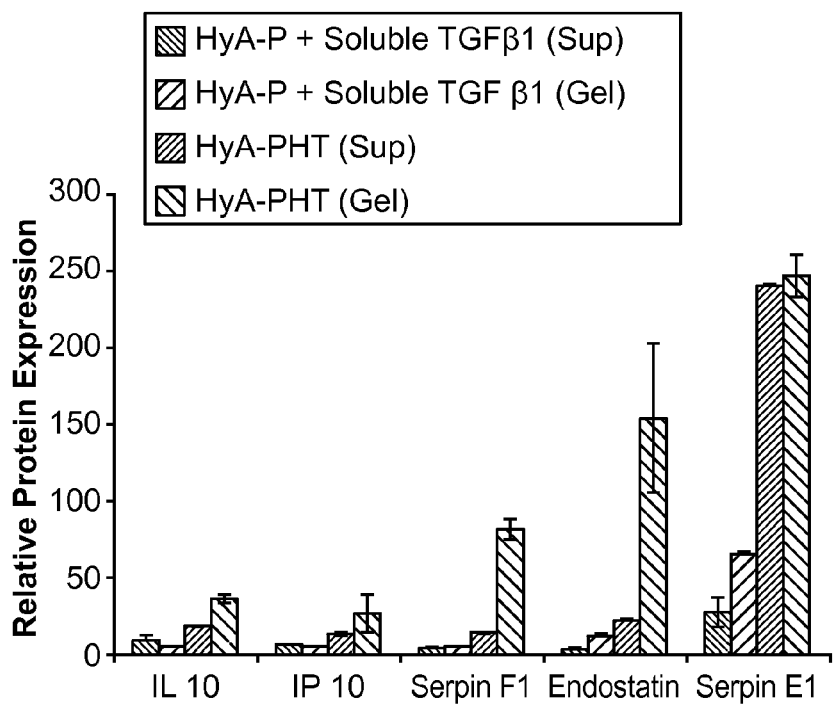

The effect of AcHyA hydrogel components on CPC trophic function was investigated. CPCs were cultured for 12 days in the four HyA hydrogel combinations used previously (i.e., HyA, HyA-P, HyA-PH and HyA-PHT) and the concentration of secreted angiogenic paracrine factors retained by the hydrogel matrix were measured (FIG. 10A-B). Only low paracrine factor expression was observed by CPCs entrained in any of the hydrogels without TGFβ1, and by contrast, the cells seeded in the HyA-PHT expressed high levels of sequestered angiogenic factors. Interestingly, the cells seeded in HyA-P and treated with soluble TGFβ1 also produced some paracrine factors, but only a limited subset relative to the HyA-PHT hydrogel and at lower expression levels in both the hydrogel and supernatant. In the absence of heparin, the differentiation of CPCs into ECs, as measured by CD31 expression and Ac-LDL uptake, and the formation of tubule structures was also diminished (FIG. 8). Taken together, these data show that HyA hydrogels can promote the trophic function of entrained CPCs, which depends not only on TGFβ1 treatment, but also on the specific presentation of TGFβ1 via its heparin-binding domain and the solid phase presentation of a unique subset of angiogenic factors subsequently synthesized by the entrained CPCs. Furthermore, the AcHyA-Heparin component sequestered the secreted paracrine factors to generate a higher localized concentration within the hydrogel.

Figure 11A:
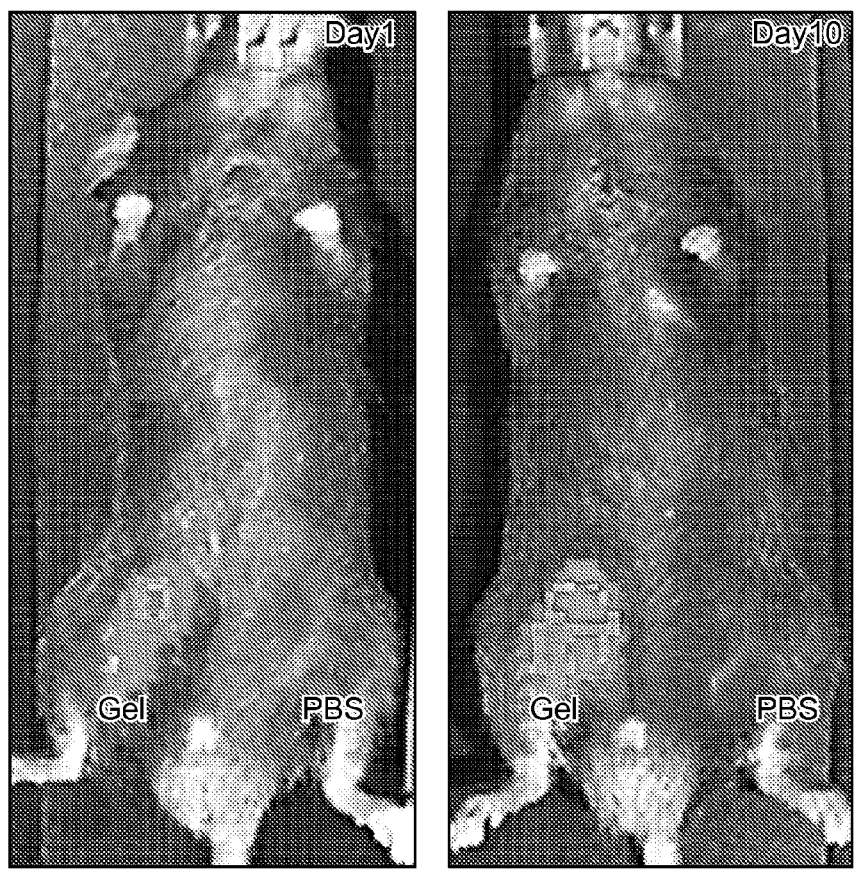
FIGS. 11A-F depict evaluation of CPC survival and neovascular function in vivo following transplantation with HyA-PHT hydrogels. Shown is (A) post-implantation of GFP-rLuc-mCPCs (500,000) into synergenic mouse hinglimbs visualized by BLI and (B) quantified over time. Also depicted are transplants after 12 days, showing (C) infiltration of host cells and host vascular network, (D) high cellular density and ECM production, (E) donor CPCs expressing GFP, and (F) vascular differentiated CD31 positive cells.
Figure 11B:
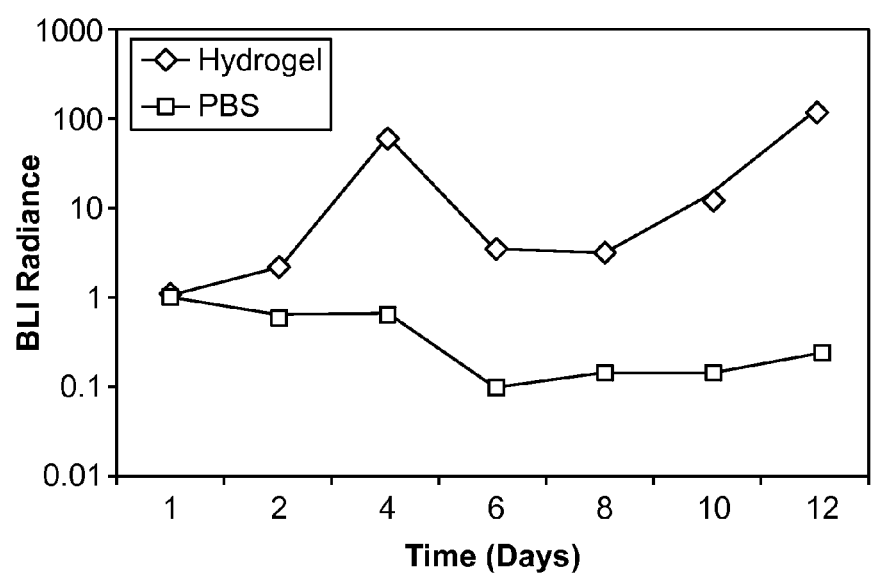
Figure 11C:
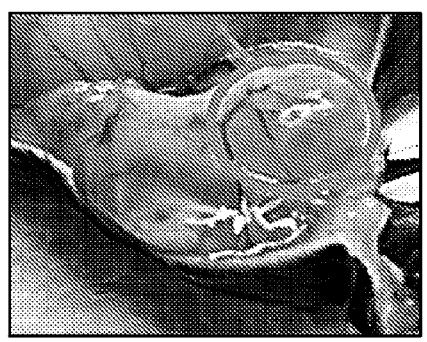
Figure 11D:
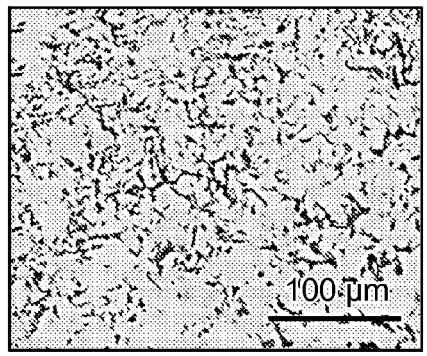
Figure 11E:
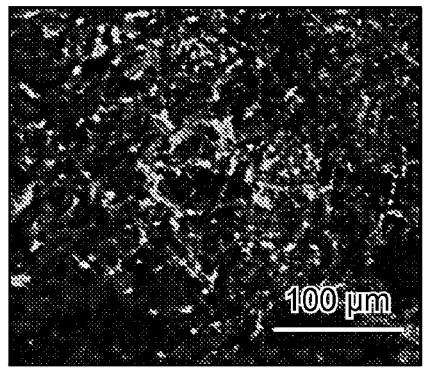
Figure 11F:
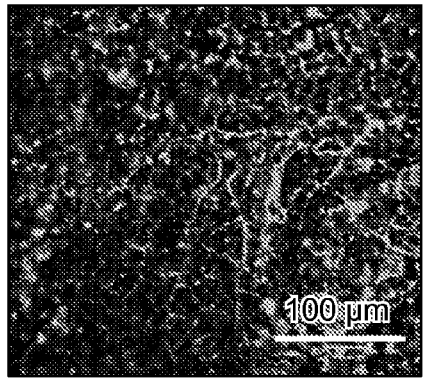

The in vivo performance of the hydrogels in promoting CPC survival, differentiation and engraftment was evaluated using a subcutaneous implantation model in syngeneic C57BL/6 mice. The CPCs, transduced with renilla luciferase (rLuc), entrained in the HyA-PHT hydrogel experienced a peak in bioluminescence (BLI) signal after 4 days followed by a steady increase in BLI signal from day 6 to day 12 (FIG. 11B). The early increase in BLI signal was anticipated due to activity that is likely to occur on the ubiquitin promoter as the CPCs recover from initial proteotoxic stresses encountered following in vivo implantation[40,41]. An overall smaller BLI signal from the control CPCs injected with saline indicated fewer cells survived, and a drop in BLI signal that never recovered, consistent with previous reports[14,42]. After 12 days, mice were sacrificed and the transplanted regions were inspected. The hydrogel in the limbs injected with HyA-PHT was easily identified in the subcutaneous tissue, and it was evident that the transplants had become integrated with the host vasculature (FIG. 11C). Immunohistochemistry analysis of the hydrogels exhibited a high cellular density, and many of the entrained cells were GFP (FIG. 11E), indicating that they were derived from the GFP CPCs. However, approximately 18% of the cells were not expressing GFP, which suggest that the HyA-PHT hydrogels were conductive to the hosts' cells, and promoted engraftment in host tissue. Endothelial cell differentiation was also verified in the hydrogel implants, as approximately 93% of the cells were positive for CD31+ (FIG. 11F). Interestingly approximately 5% of the CD31+ cells were negative for GFP, and thus it is likely that these were endothelial cells recruited from the host vasculature. Finally, extracellular matrix production was evaluated within and around the implants using Masson's trichrome stain (FIG. 11D). There was evidence of collagen development inside the hydrogel, suggesting that the cells were remodeling the hydrogel and depositing their own extracellular matrix. Collectively these observations show that the HyA-PHT implant encouraged neovascularization and integration with the host tissue, and its effects were mediated on both the transplanted CPCs and the neighboring host cells.

Figure 12A:
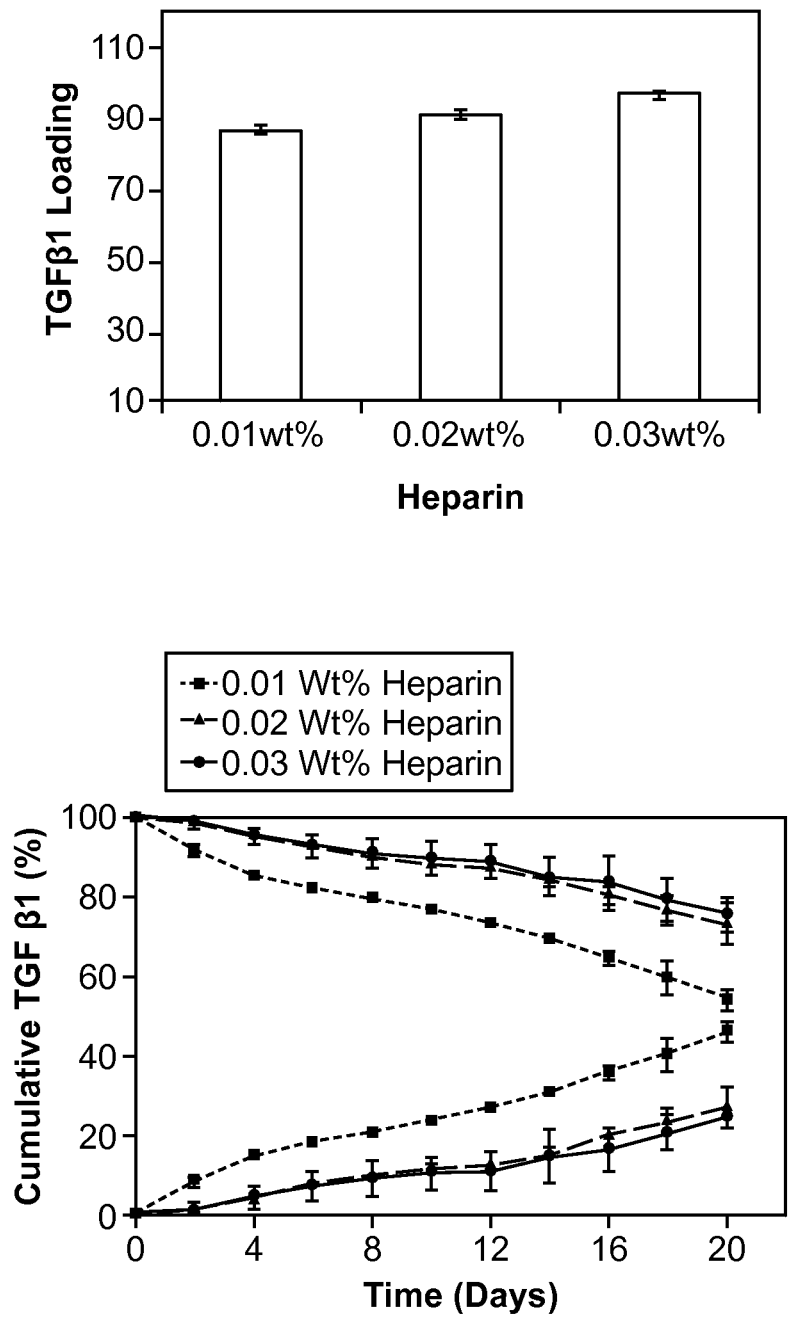
FIGS. 12A-C depict the percentage of TGFβ1 retained by the hydrogel as a function of the weight percentage of incorporated heparin and concentration of TGFβ1 at (A) 10 nM, (B) 20 nM, and (C) 40 nM.
Figure 12B:
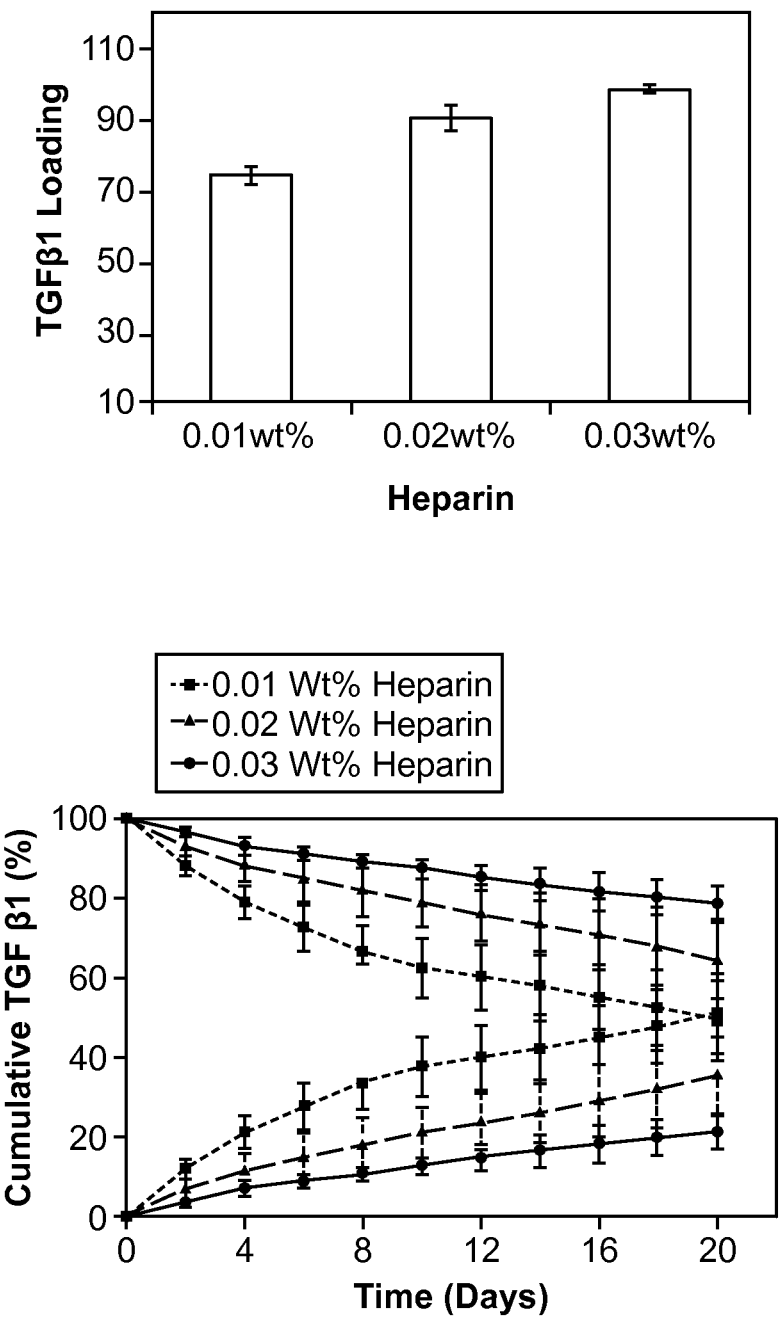
Figure 12C:
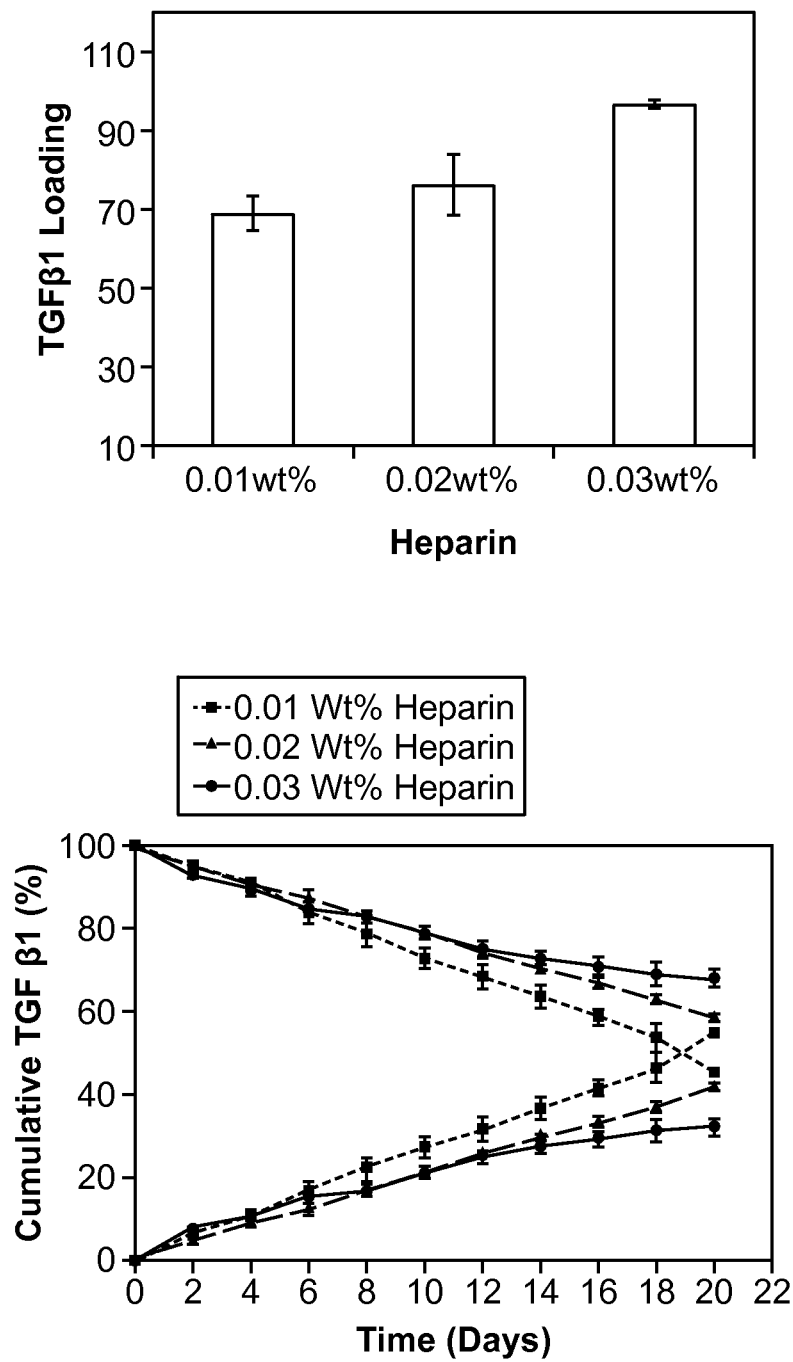

Example 2: Growth Factor Sequestering and Presenting Hydrogels Promote Survival and Engraftment of Transplanted Stem Cells TGFβ1 Retention and Weight Percentage of Heparin The percentage of TGFβ1 retained by the hydrogel is dependent on the weight percentage of incorporated heparin at 10 nM (a), 20 nM (b), and 40 nM concentration of TGFβ1, as determined by ELISA (FIG. 12A-C). Depending on the weight percentage of heparin present, HyA hydrogels (0.03 wt. % haparin) retain over 70% of the TGFβ1 for up to 20 days. Lower 0.01 wt. % of heparin generated hydrogels with slow and nearly zero order release kinetics.

Hydrogel Characteristics

Figure 13A:
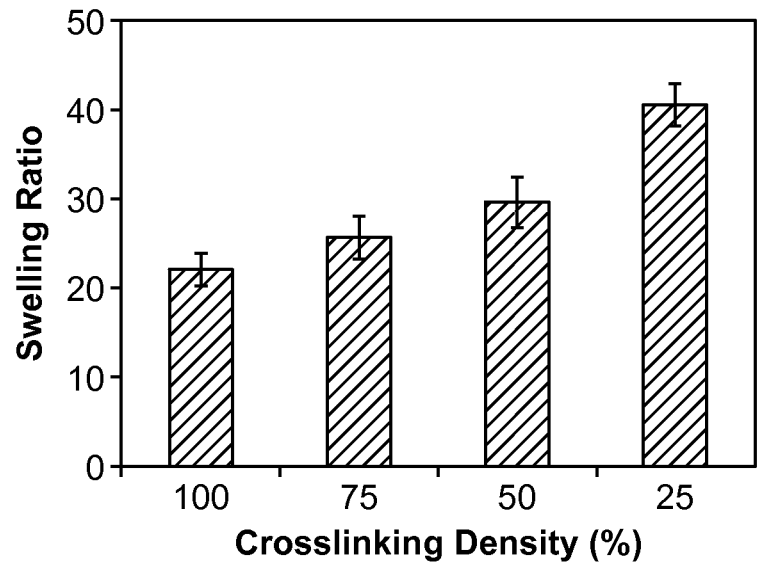
FIGS. 13A-B depict sol fraction and swelling ratios of the hydrogel as a function of crosslinking density and weight percentages HyA.
Figure 13A:
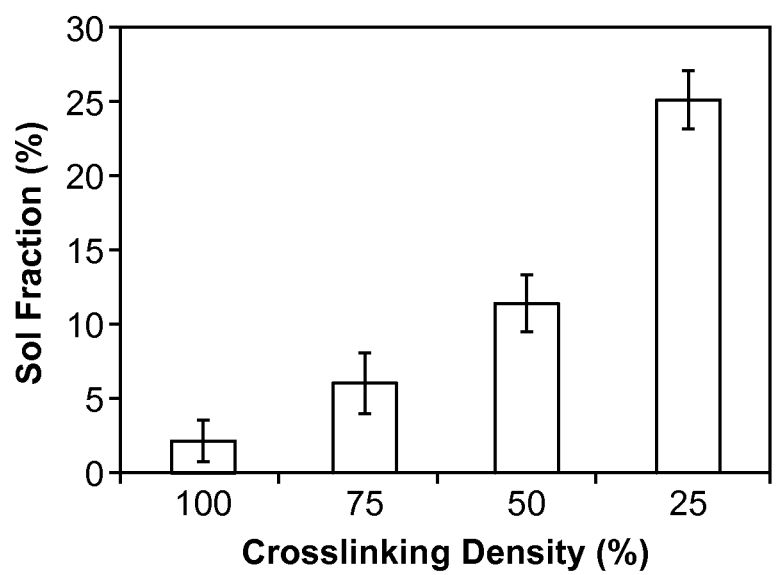
Figure 13B:
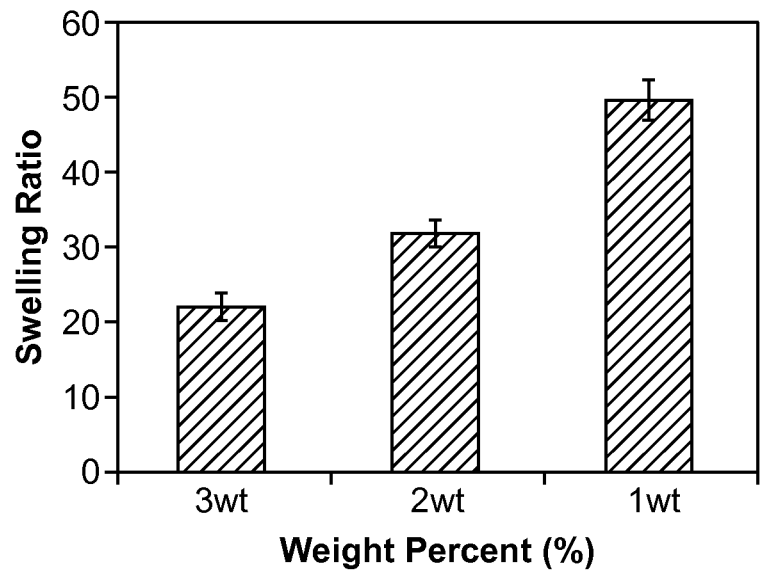
Figure 13B:
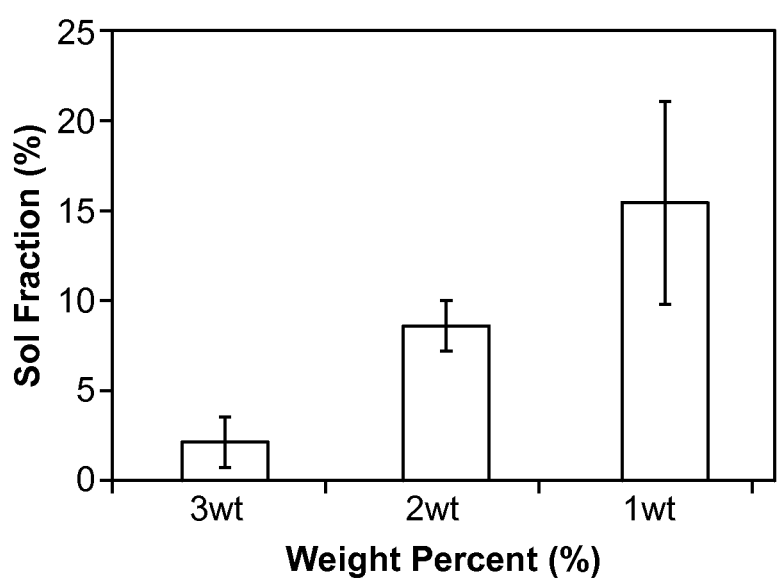

Sol fraction and swelling ratios of the hydrogel were determined (FIG. 13A), at the various crosslinking densities (defined as moles of thiol on the peptide cross linker compared to moles of acrylate groups on AcHyA) with constant weight percentage (3 wt %) of the hydrogel and (FIG. 13B), at various weight percentages HyA with constant crosslinking density (100% crosslinking density). Three repeating measurements were performed on each sample.

CPC Differentiation within Hydrogels

Figure 14A:
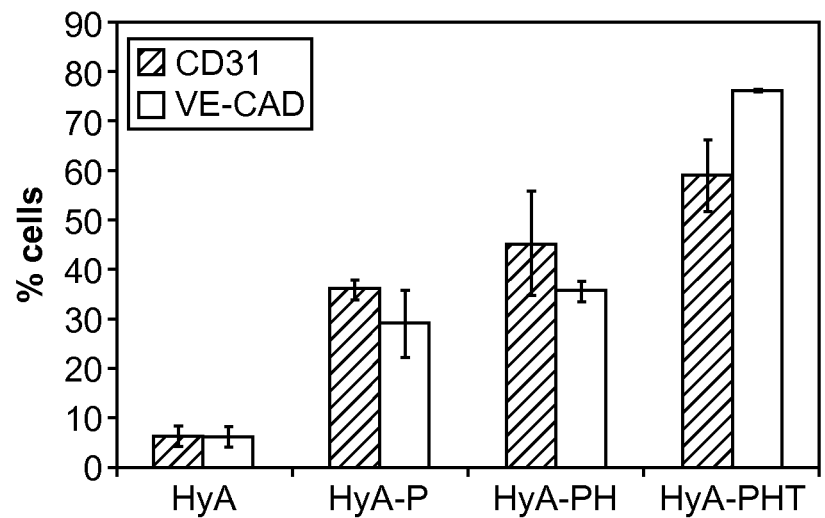
FIGS. 14A-B depict endothelial cell differentiation of CPCs within hydrogels as assessed by flow cytometry and immunochemistry.
Figure 14A:
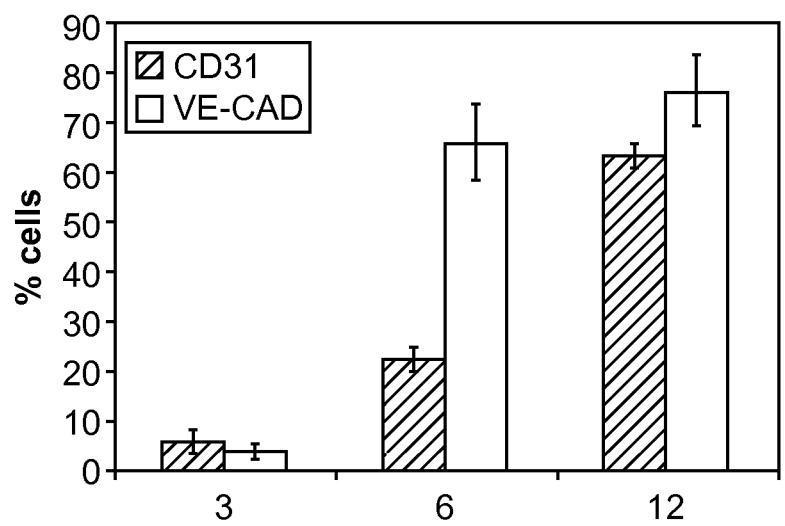
Figure 14B:
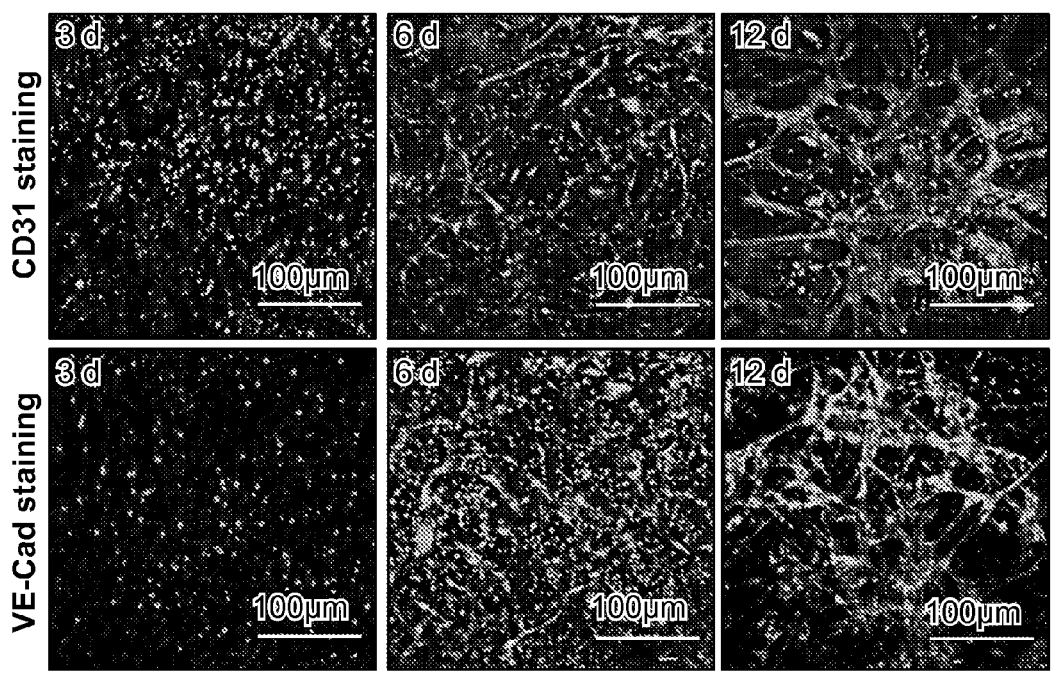

CPCs differentiate into endothelial cells within the hydrogels. (FIG. 14A), The percentage of differentiated endothelial cells within the different HyA hydrogels expressing CD31 and VE-cadherin was quantitatively measured using flow cytometry. The time dependency of EC differentiation was also observed by measuring the expression of these cell surface markers over the 12 days following CPC seeding into the HyA-PHT hydrogels. (FIG. 14B) Endothelial cell differentiation in situ was assessed using immunocytochemistry to identify CD31 and VE-cadherin positive cells within the HyA-PHT hydrogels, where network structures resembling vascular morphology were observed within 12 days.

Figure 15A:
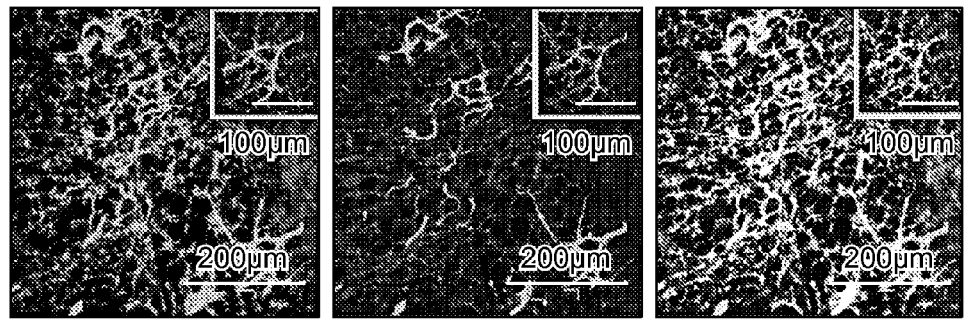
FIGS. 15A-C depict capillary-like structures formed in vivo in HyA-PHT gels as confirmed by (A) perfusion of isolectin from *Griffonia simplicifolia* and immunostaining of (B) endomucin and (C) CD31.
Figure 15B:
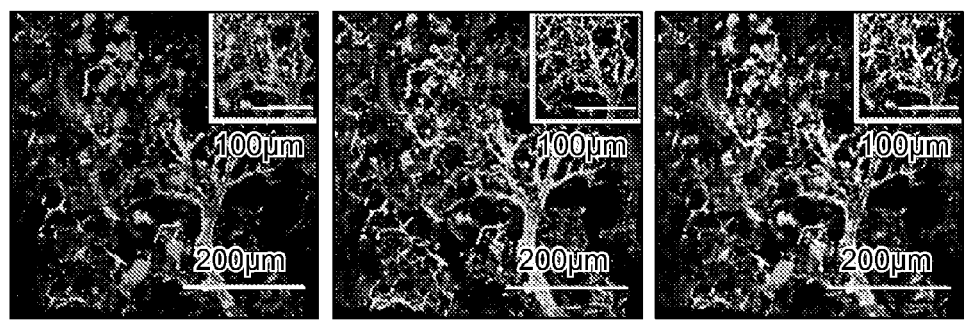
Figure 15C:
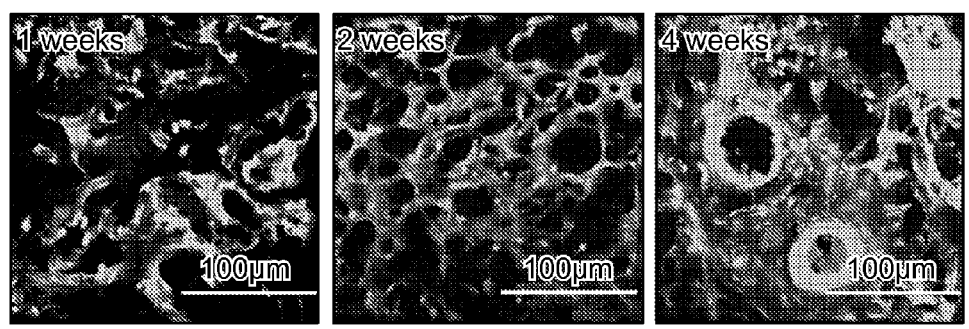

During Terminal Differentiation, the Cells Begin to Form Capillary-Like Structures HyA-PHT gels can encourage the formation of mature capillary structures at 32 days. To visualize angiogenesis in the CPC/HyA-PHT hydrogel after 16 days of implantation in the hindslimb of mice, AlexaFluor 568 conjugated isolectin GS-IB4 from *Griffonia simplicifolia* (Invitrogen) was delivered through left ventricle immediately after mice were euthanized and cryosection (50 μm) of explants were visualized under the confocal microscope. FIGS. 15A and 15B show CPC/HyA-PHT implants removed after 16 days and stained for vascularization. In FIG. 15A the left image is isolectin stained vessels and nuclei; the center image is isolectin stained vessels and GFP positive CPCs; the right image is isolectin stained vessels and GFP positive CPCs, and nuclei. In FIG. 15B the left image is endomucin and nuclei; the center image is endomucin and GFP positive CPCs; and the right image is endomucin stained and GFP positive CPCs, and nuclei. FIG. 15C shows cells visualized using CD31, a cell surface marker that is presented on the surface of cells during endothelial cell differentiation.

HyA-PHT Promote Cell Survival

Figure 16:
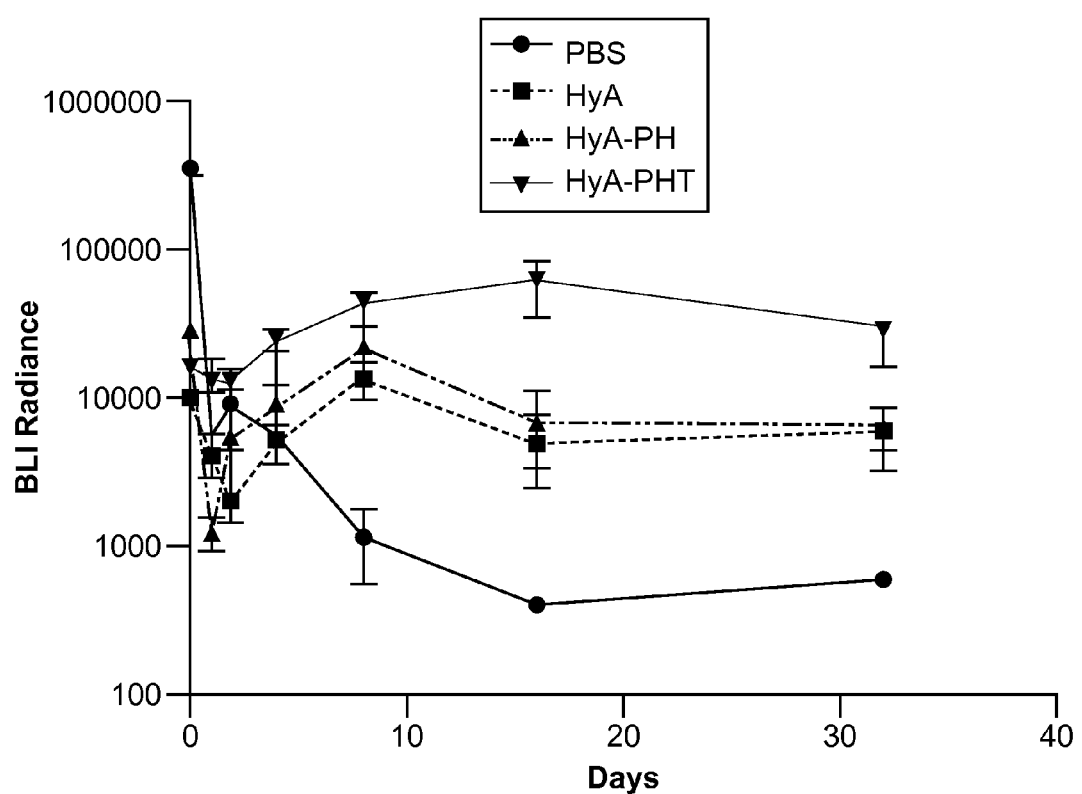
FIG. 16 depicts in vivo CPC survival over time for various hydrogels and control as determined by measuring radiance of CPCs transplanted into mouse hind limbs.

The HyA-PHT hydrogels promote cardiac progenitor cell survival in vivo (FIG. 16). The ~500,000 CPC were injected into the mouse hindlimbs using either the HyA, HyA-PH, and HyA-PHT gels, or sterile saline (PBS) as a control. The CPCs were transduced with Firefly luciferase, and this reporter was constitutively expressed and measured in vivo as an indicator of cell survival. We measured the radiance generated by the transplanted CPC in the mouse hind limbs for 32 days. Within 2-4 days of the injection, the cells transplanted using saline could not be detected, whereas cell increased when transplanted using HyA, HyA-PH until 8 days, then decreased and remain same over 32 days. However, the population of cells transplanted using the HyA-PHT hydrogels increased over 16 days, maintain similar cell number in HyA-PHT by 32 days. The HyA-PHT promote cell survival, whereas the radiance generated by the CPCs transplanted with saline declined over time.

REFERENCES

1. Min, J.-Y. et al. Significant improvement of heart function by cotransplantation of human mesenchymal stem cells and fetal cardiomyocytes in post-infarcted pigs. *Ann Thorac Surg* 74, 1568-1575 (2002).
2. Matsuura, K. et al. Transplantation of cardiac progenitor cells ameliorates cardiac dysfunction after myocardial infarction in mice. *The Journal of clinical investigation* 119, 2204-2217 (2009).
3. Mizuno, Y. et al. Generation of skeletal muscle stem/progenitor cells from murine induced pluripotent stem cells. *FASEB journal: official publication of the Federation of American Societies for Experimental Biology* 24, 2245-2253 (2010).
4. Liu, H., Kim, Y., Sharkis, S., Marchionni, L. & Jang, Y. Y. In vivo liver regeneration potential of human induced pluripotent stem cells from diverse origins. *Science translational medicine* 3, 82ra39 (2011).
5. Toma, C., Pittenger, M. F., Cahill, K. S., Byrne, B. J. & Kessler, P. D. Human mesenchymal stem cells differentiate to a cardiomyocyte phenotype in the adult murine heart. *Circulation* 105, 93-98 (2002).
6. Perin, E. C. et al. Transendocardial, autologous bone marrow cell transplantation for severe, chronic ischemic heart failure. *Circulation* 107, 2294-2302 (2003).
7. Smith, R. R. et al. Regenerative potential of cardiosphere-derived cells expanded from percutaneous endomyocardial biopsy specimens. *Circulation* 115, 896-908 (2007).
8. Beauchamp, J. R., Morgan, J. E., Pagel, C. N. & Partridge, T. A. Dynamics of myoblast transplantation reveal a discrete minority of precursors with stem cell-like properties as the myogenic source. *J Cell Biol* 144, 1113-1122 (1999).
9. Mitkari, B. et al. Intra-arterial infusion of human bone marrow-derived mesenchymal stem cells results in transient localization in the brain after cerebral ischemia in rats. *Experimental neurology* 239, 158-162 (2013).
10. Suzuki, K. et al. Role of interleukin-1beta in acute inflammation and graft death after cell transplantation to the heart. *Circulation* 110, 11219-224 (2004).
11. Fang, J. et al. Stimulation of new bone formation by direct transfer of osteogenic plasmid genes. *Proc. Natl. Acad. Sci* 93, 5753-5758 (1996).
12. Beauchamp, J. R., Morgan, J. E., Pagel, C. N. & Partridge, T. A. Dynamics of myoblast transplantation reveal a discrete minority of precursors with stem cell-like properties as the myogenic source. *The Journal of cell biology* 144, 1113-1122 (1999).
13. Mora-Lee, S. et al. Therapeutic effects of hMAPC and hMSC transplantation after stroke in mice. *PloS one* 7, e43683 (2012).
14. Li, Z. et al. Differentiation, survival, and function of embryonic stem cell derived endothelial cells for ischemic heart disease. *Circulation* 116, 146-54 (2007).
15. Gao, J. et al. The use of chitosan based hydrogel for enhancing the therapeutic benefits of adipose-derived MSCs for acute kidney injury. *Biomaterials* 33, 3673-3681 (2012).

16. Lesman, A. et al. Transplantation of a tissue-engineered human vascularized cardiac muscle. *Tissue engineering. Part A* 16, 115-125 (2010).
17. Parisi-Amon, A., Mulyasasmita, W., Chung, C. & Heilshorn, S. C. Protein-engineered injectable hydrogel to improve retention of transplanted adipose-derived stem cells. *Advanced healthcare materials* 2, 428-432 (2013).
18. Xiong, Q. et al. A fibrin patch-based enhanced delivery of human embryonic stem cell-derived vascular cell transplantation in a porcine model of postinfarction left ventricular remodeling. *Stem cells* 29, 367-375 (2011).
19. Unterman, S. A. et al. Hyaluronic acid-binding scaffold for articular cartilage repair. *Tissue engineering. Part A* 18, 2497-2506 (2012).
20. Wall, S. T., Yeh, C. C., Tu, R. Y., Mann, M. J. & Healy, K. E. Biomimetic matrices for myocardial stabilization and stem cell transplantation. *J Biomed Mater Res A* 95, 1055-1066 (2010).
21. Kim, J. et al. Bone regeneration using hyaluronic acid-based hydrogel with bone morphogenic protein-2 and human mesenchymal stem cells. *Biomaterials* 28, 1830-1837 (2007).
22. Freudenberg, U. et al. A star-PEG-heparin hydrogel platform to aid cell replacement therapies for neurodegenerative diseases. *Biomaterials* 30, 5049-5060 (2009).
23. Craig, E. A., Parker, P., Austin, A. F., Barnett, J. V. & Camenisch, T. D. Involvement of the MEKK1 signaling pathway in the regulation of epicardial cell behavior by hyaluronan. *Cellular Signalling* 22, 968-976 (2010).
24. Khetan, S., Katz, J. S. & Burdick, J. A. Sequential crosslinking to control cellular spreading in 3-dimensional hydrogels. *Soft Matter* 5 (2009).
25. Engler, A. J., Sen, S., Sweeney, H. L. & Discher, D. E. Matrix Elasticity Directs Stem Cell Lineage Specification. *Cell* 126, 677-689 (2006).
26. Shapira-Schweitzer, K. & Seliktar, D. Matrix stiffness affects spontaneous contraction of cardiomyocytes cultured within a PEGylated fibrinogen biomaterial. *Acta biomaterialia* 3, 33-41 (2007).
27. Saha, K. et al. Substrate modulus directs neural stem cell behavior. *Biophys J* 95, 4426-4438 (2008).
28. Saha, K., Pollock, J. F., Schaffer, D. V. & Healy, K. E. Designing synthetic materials to control stem cell phenotype. *Current Opinion in Chemical Biology* 11, 381-387 (2007).
29. Chung, E. H. et al. Biomimetic artificial ECMs stimulate bone regeneration. *J Biomed Mater Res A* 79, 815-826 (2006).
30. Trappmann, B. et al. Extracellular-matrix tethering regulates stem-cell fate. 11, 642-649 (2012).
31. Khetan, S., Katz, J. S. & Burdick, J. A. Sequential crosslinking to control cellular spreading in 3-dimensional hydrogels. *Soft Matter* 5, 1601-1606 (2009).
32. Kraehenbuehl, T. P. et al. Three-dimensional extracellular matrix-directed cardioprogenitor differentiation: systematic modulation of a synthetic cell-responsive PEG-hydrogel. *Biomaterials* 29, 2757-2766 (2008).
33. Raeber, G. P., Lutolf, M. P. & Hubbell, J. A. Molecularly Engineered PEG Hydrogels: A Novel Model System for Proteolytically Mediated Cell Migration. *Biophysical Journal* 89, 1374-1388 (2005).
34. Rezania, A., Thomas, C. H., Branger, A. B., Waters, C. M. & Healy, K. E. The detachment strength and morphology of bone cells contacting materials modified with a peptide sequence found within bone sialoprotein. *Journal of biomedical materials research* 37, 9-19 (1997).
35. Goumans, M.-J. et al. TGF-beta1 induces efficient differentiation of human cardiomyocyte progenitor cells into functional cardiomyocytes in vitro. *Stem Cell Research* 1, 138-149 (2008).
36. Bein, K., Odell-Fiddler, E. T. & Drinane, M. Role of TGF-beta1 and JNK signaling in capillary tube patterning. *American Journal of Physiology—Cell Physiology* 287, C1012-C1022 (2004).
37. Goumans, M.-J., Liu, Z. & ten Dijke, P. TGF-[beta] signaling in vascular biology and dysfunction. *Cell Res* 19, 116-127 (2009).
38. LÓpez-Novoa, J. M. & Bernabeu, C. The physiological role of endoglin in the cardiovascular system. *American Journal of Physiology—Heart and Circulatory Physiology* 299, H959-H974 (2010).
39. Ye, J. et al. Sca-1+ Cardiosphere-Derived Cells Are Enriched for Is11-Expressing Cardiac Precursors and Improve Cardiac Function after Myocardial Injury. *PLoS ONE* 7, e30329 (2012).
40. Dantuma, N. P. & Lindsten, K. Stressing the ubiquitin-proteasome system. *Cardiovascular research* 85, 263-271 (2010).
41. Workman, P. & Davies, F. E. A stressful life (or death): combinatorial proteotoxic approaches to cancer-selective therapeutic vulnerability. *Oncotarget* 2, 277-280 (2011).
42. Liu, Z. et al. The influence of chitosan hydrogel on stem cell engraftment, survival and homing in the ischemic myocardial microenvironment. *Biomaterials* 33, 3093-3106 (2012).
43. Jha, A. K. et al. Structural Analysis and Mechanical Characterization of Hyaluronic Acid-Based Doubly Cross-Linked Networks. *Macromolecules* 42, 537-546 (2009).
44. Voytik-Harbin, S., Brightman, A., Waisner, B., Lamar, C. & Badylak, S. Application and evaluation of the alamar-blue assay for cell growth and survival of fibroblasts. *In Vitro Cellular & Developmental Biology—Animal* 34, 239-246 (1998).
45. Al-Nasiry, S., Geusens, N., Hanssens, M., Luyten, C. & Pijnenborg, R. The use of Alamar Blue assay for quantitative analysis of viability, migration and invasion of choriocarcinoma cells. *Human Reproduction* 22, 1304-1309 (2007).
46. Jha, A. K., Malik, M. S., Farach-Carson, M. C., Duncan, R. L. & Jia, X. Hierarchically structured, hyaluronic acid-based hydrogel matrices via the covalent integration of microgels into macroscopic networks. *Soft matter* 6, 5045-5055 (2010).

What is claimed is:

1. A hydrogel cell matrix comprising:
   a) a plurality of hydrogel polymers;
   b) a cell adhesion peptide conjugated to one or more hydrogel polymers;
   c) a factor release molecule conjugated to one or more hydrogel polymers, wherein the factor release molecule is present in the matrix at a density of 0.01 weight % to 0.03 weight %; and
   d) a proteolytically cleavable cross-linker peptide that links one or more hydrogel polymers of the plurality of hydrogel polymers to another hydrogel polymer of the plurality, wherein the cross-linker peptide is CQPQGLAKC (SEQ ID NO:46), and
   wherein the matrix has an elastic modulus of from about 15 Pa to 850 Pa.

2. The hydrogel cell matrix of claim 1, wherein the hydrogel polymer is a hyaluronic acid (HyA) polymer or an acrylated hyaluronic acid (HyA) polymer.

3. The hydrogel cell matrix of claim 1, wherein the cell adhesion peptide and the factor release molecule are conjugated to the same hydrogel polymer.

4. The hydrogel cell matrix of claim 1, wherein the cell adhesion peptide and the factor release molecule are conjugated to different hydrogel polymers.

5. The hydrogel cell matrix of claim 1, wherein the cell adhesion peptide comprises the amino acid sequence RGD.

6. The hydrogel cell matrix of claim 5, wherein the cell adhesion peptide comprises the amino acid sequence CGGNGEPRGDTYRAY (SEQ ID NO:1).

7. The hydrogel cell matrix of claim 1, wherein the factor release molecule is heparin.

8. The hydrogel cell matrix of claim 1, further comprising a growth factor non-covalently bound to the factor release molecule, wherein the factor release molecule allows for the release, presentation, or release and presentation of the growth factor.

9. The hydrogel cell matrix of claim 8, wherein the growth factor is transforming growth factor-β (TGF-β).

10. The hydrogel cell matrix of claim 8, wherein the growth factor was secreted by a cell cultured on the hydrogel cell matrix.

11. The hydrogel cell matrix of claim 1, wherein the cross-linker is a thiolated cross linker peptide.

12. A hydrogel cell matrix system comprising the hydrogel cell matrix of claim 1 and a stem cell or progenitor cell encapsulated in the matrix.

13. The hydrogel cell matrix system of claim 12, wherein the system comprises a progenitor cell.

14. The hydrogel cell matrix system of claim 13, wherein the progenitor cell is a cardiac progenitor cell.

15. A method of making a hydrogel cell matrix comprising the steps of:
   (a) conjugating cell adhesion peptides to a first population of hydrogel polymers;
   (b) conjugating factor release molecules to a second population of hydrogel polymers; and
   (c) conjugating the first population of hydrogel polymers to the second population of hydrogel polymers using proteolytically cleavable cross-linker peptides,
   thereby producing a hydrogel cell matrix.

16. The method of claim 15, further comprising, after step (b), a step of contacting the factor release molecules with a growth factor, wherein the growth factor non-covalently binds to the factor release molecules, thereby producing a growth factor contacted hydrogel cell matrix.

17. The method of claim 16, further comprising culturing a cell on the growth factor contacted hydrogel cell matrix, wherein factors secreted by the cell non-covalently bind to the factor release molecules.

18. The method of claim 15, further comprising, after step (b), culturing a cell in the presence of the factor release molecules, wherein factors secreted by the cell non-covalently bind to the factor release molecules.

19. The method of claim 15, further comprising, after step (c), culturing a cell on the hydrogel cell matrix, wherein factors secreted by the cell non-covalently bind to the factor release molecules.

20. A method of introducing a hydrogel cell matrix into a mammalian subject, comprising, prior to gelation, injecting the hydrogel cell matrix of claim 1 into the mammalian subject.

21. The method of claim 20, wherein the hydrogel cell matrix comprises a growth factor non-covalently bound to the factor release molecule, wherein the factor release molecule allows for the release, presentation, or release and presentation of the growth factor.

22. The method of claim 21, wherein the growth factor was secreted by a cell cultured on the hydrogel cell matrix.

23. The method of claim 20, wherein the hydrogel cell matrix comprises a stem cell or progenitor cell.

24. The hydrogel cell matrix of claim 1, wherein the hydrogel polymer is present in the matrix at a density of from 1 weight % to 3 weight %.

25. The hydrogel cell matrix of claim 1, wherein the crosslinking density is from about 25% to 100%.

* * * * *